(12) United States Patent
Perroud et al.

(10) Patent No.: US 8,585,916 B2
(45) Date of Patent: Nov. 19, 2013

(54) MICROPORES AND METHODS OF MAKING AND USING THEREOF

(75) Inventors: Thomas D. Perroud, San Jose, CA (US); Kamlesh D. Patel, Dublin, CA (US); Robert J. Meagher, Mountain House, CA (US)

(73) Assignee: Sandia Corporation, Albuquerque, NM (US)

( * ) Notice: Subject to any disclaimer, the term of this patent is extended or adjusted under 35 U.S.C. 154(b) by 589 days.

(21) Appl. No.: 12/812,986

(22) PCT Filed: Jan. 21, 2009

(86) PCT No.: PCT/US2009/031516
§ 371 (c)(1),
(2), (4) Date: Jul. 15, 2010

(87) PCT Pub. No.: WO2009/126352
PCT Pub. Date: Oct. 15, 2009

(65) Prior Publication Data
US 2011/0024368 A1    Feb. 3, 2011

Related U.S. Application Data

(60) Provisional application No. 61/062,401, filed on Jan. 24, 2008, provisional application No. 61/062,545, filed on Jan. 24, 2008, provisional application No. 61/142,780, filed on Jan. 6, 2009.

(51) Int. Cl.
*B31D 3/00*    (2006.01)

(52) U.S. Cl.
USPC ............... 216/56; 216/2; 216/41; 216/83

(58) Field of Classification Search
None
See application file for complete search history.

(56) References Cited

U.S. PATENT DOCUMENTS

| | | | |
|---|---|---|---|
| 5,654,238 A | 8/1997 | Cronin et al. | |
| 6,093,330 A * | 7/2000 | Chong et al. | ............ 216/2 |
| 6,432,290 B1 | 8/2002 | Harrison et al. | |
| 6,629,820 B2 | 10/2003 | Kornelsen | |
| 6,632,619 B1 | 10/2003 | Harrison et al. | |
| 6,706,203 B2 | 3/2004 | Barth et al. | |
| 6,824,663 B1 | 11/2004 | Boone | |

(Continued)

FOREIGN PATENT DOCUMENTS

| | | |
|---|---|---|
| JP | 2006-181670 | 7/2006 |
| JP | 2007-098488 | 4/2007 |

(Continued)

OTHER PUBLICATIONS

M. Madou, Fundamentals of Microfabrication, CRC Press, Boca Raton, 1997, p. 166.*

(Continued)

*Primary Examiner* — Lan Vinh
*Assistant Examiner* — Jiong-Ping Lu
(74) *Attorney, Agent, or Firm* — Smith, Gambrell & Russell, LLP

(57) ABSTRACT

Disclosed herein are methods of making micropores of a desired height and/or width between two isotropic wet etched features in a substrate which comprises single-level isotropic wet etching the two features using an etchant and a mask distance that is less than 2× a set etch depth. Also disclosed herein are methods using the micropores and microfluidic devices comprising the micropores.

15 Claims, 16 Drawing Sheets

(56) References Cited

U.S. PATENT DOCUMENTS

| | | |
|---|---|---|
| 6,833,542 B2 | 12/2004 | Wang et al. |
| 6,875,619 B2 | 4/2005 | Blackburn |
| 6,900,021 B1 | 5/2005 | Harrison et al. |
| 7,077,175 B2 | 7/2006 | Yin et al. |
| 7,094,354 B2 | 8/2006 | Pugia et al. |
| 7,125,667 B2 | 10/2006 | Blumenfeld et al. |
| 7,157,274 B2 | 1/2007 | Böhm et al. |
| 7,171,975 B2 | 2/2007 | Moon et al. |
| 7,220,592 B2 | 5/2007 | Rakestraw et al. |
| 7,244,961 B2 | 7/2007 | Jovanovich et al. |
| 7,296,592 B2 | 11/2007 | Rehm et al. |
| 7,312,611 B1 | 12/2007 | Harrison et al. |
| 7,351,315 B2 | 4/2008 | Klocke et al. |
| 2002/0197167 A1 | 12/2002 | Kornelsen |
| 2003/0178075 A1 | 9/2003 | Moon et al. |
| 2003/0217923 A1 | 11/2003 | Harrison et al. |
| 2004/0178071 A1 | 9/2004 | Harrison et al. |
| 2004/0209354 A1 | 10/2004 | Mathies et al. |
| 2004/0235181 A1 | 11/2004 | Arnold et al. |
| 2004/0265172 A1 | 12/2004 | Pugia et al. |
| 2005/0009101 A1 | 1/2005 | Blackburn |
| 2005/0050767 A1 | 3/2005 | Hanson et al. |
| 2005/0207940 A1 | 9/2005 | Butler et al. |
| 2005/0224134 A1 | 10/2005 | Yin et al. |
| 2006/0014360 A1 | 1/2006 | Matsumoto |
| 2006/0060767 A1 | 3/2006 | Wang et al. |
| 2006/0222635 A1 | 10/2006 | Centanni et al. |
| 2007/0099289 A1 | 5/2007 | Irimia et al. |
| 2007/0170056 A1 | 7/2007 | Arnold et al. |
| 2007/0243523 A1 | 10/2007 | Ionescu-Zanetti et al. |
| 2007/0248958 A1 | 10/2007 | Jovanovich et al. |
| 2007/0272309 A1 | 11/2007 | Rehm et al. |
| 2008/0014576 A1 | 1/2008 | Jovanovich et al. |
| 2008/0020368 A1 | 1/2008 | Yang et al. |
| 2008/0020370 A1 | 1/2008 | Philpott et al. |
| 2008/0138848 A1 | 6/2008 | Li et al. |
| 2008/0179180 A1 | 7/2008 | McHugh et al. |
| 2008/0182136 A1 | 7/2008 | Arnold et al. |

FOREIGN PATENT DOCUMENTS

| | | |
|---|---|---|
| WO | 03/044164 A2 | 5/2003 |
| WO | 03/044164 A3 | 5/2003 |
| WO | 03/068672 A2 | 8/2003 |
| WO | 03/068672 A3 | 8/2003 |
| WO | 2005/001896 A2 | 1/2005 |
| WO | 2005/001896 A3 | 1/2005 |
| WO | 2005/028108 | 3/2005 |
| WO | 2005/096751 A2 | 10/2005 |
| WO | 2005/096751 A3 | 10/2005 |
| WO | 2006/007701 A1 | 1/2006 |
| WO | 2006/019500 A2 | 2/2006 |
| WO | 2006/019500 A3 | 2/2006 |
| WO | 2006/032044 A2 | 3/2006 |
| WO | 2006/032044 A3 | 3/2006 |
| WO | 2007/087632 A2 | 8/2007 |
| WO | 2007/087632 A3 | 8/2007 |

OTHER PUBLICATIONS

International Search Report for Application No. PCT/US2009/031515 mailed Oct. 28, 2009.

International Search Report for Application No. PCT/US2009/031516 mailed Oct. 30, 2009.

Tan et al., "A trap-and-release integrated microfluidic system for dynamic microarray applications", PNAS, Jan. 2007, 104(4), pp. 1146-1151.

Huh et al., "Gravity-Driven Microfluidic Particle Sorting Device with Hydrodynamic Separation Amplification", Anal. Chem., 2007, 79, 1369-1376.

Ohta et al., "Dynamic Cell and Microparticle Control via Optoelectronic Tweezers", Journal of Microelectromechanical Systems, Jun. 2007, vol. 16, No. 3, pp. 491-499.

Fu et al., "Electrokinetically driven microflow cytometers with integrated fiber optics for on-line cell/particle detection", Analytica Chimica Acta 507, 2004, pp. 163-169.

Shah et al., "A microfluidic system to capture single cells", Jun. 21, 2007, MIC—Depart. of Micro and Nanotechnology, DTU bldg. 345 east Technical University of Denmark, DK-2800 Kongens Lyngby, Denmark, pp. 1-5.

Shuler et al., "Hydrodynamic Focusing and Electronic Cell-Sizing Techniques", Applied Microbiology, Sep. 1972, 24(3), pp. 384-388.

Tu et al., "Microfluidic cell analysis and sorting using photonic forces", Optical Trapping and Optical Micromanipulation, Proceedings of SPIE, 2004 vol. 5514, pp. 774-785.

Wang et al., "Microfluidic sorting of mammalian cells by optical force switching", Nature Biotechnology, Jan. 2005, vol. 23, No. 1, pp. 83-87.

Di Carlo et al., "Continuous inertial focusing, ordering, and separation of particles in microchannels", PNAS, Nov. 27, 2007, vol. 104, No. 48, pp. 18892-18897.

Williams et al., Etch Rates for Micromachining Processing—Part II, Journal of Microelectromechinical Systems, Dec. 2003, vol. 12, No. 6, pp. 761-778.

Fu et al., "A high-discernment microflow cytometer with microweir structure", Electrophoresis, 2008, 29, pp. 1874-1880.

* cited by examiner

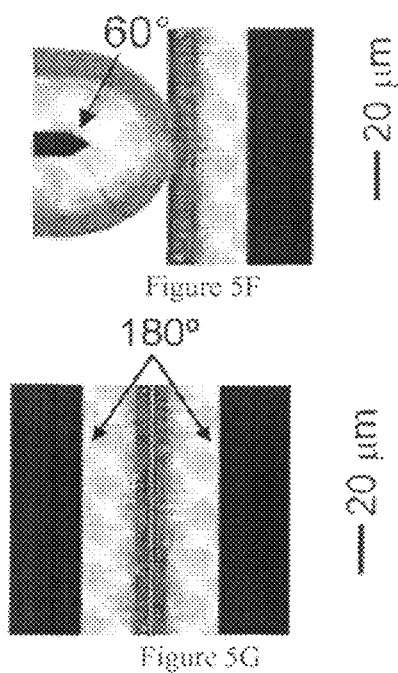

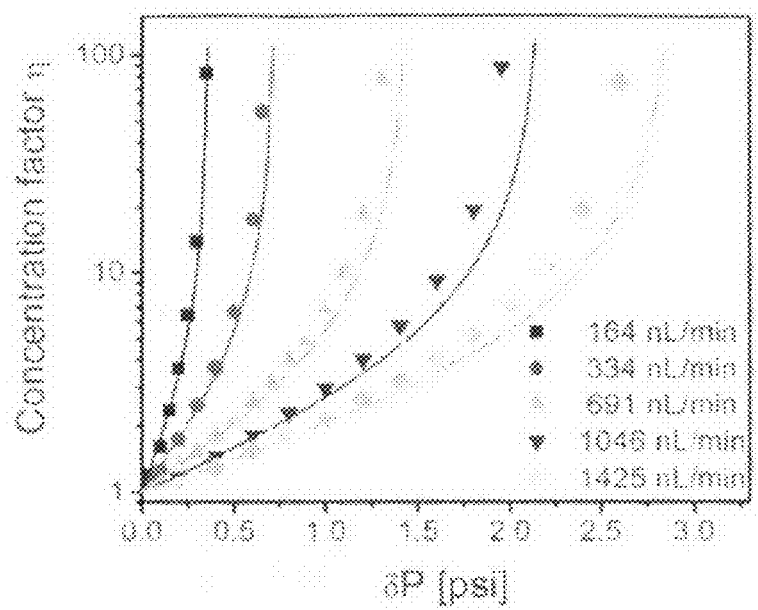
Figure 7G
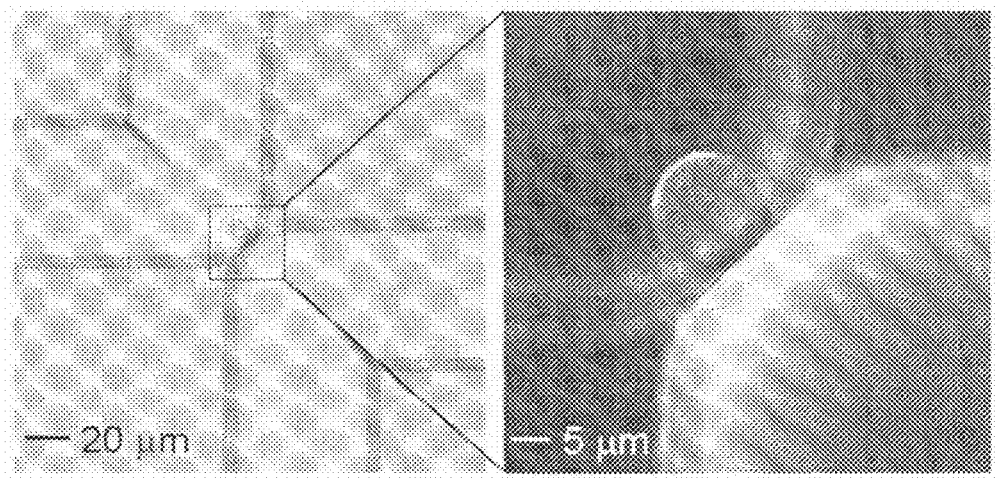
Figure 8A                    Figure 8B

MICROPORES AND METHODS OF MAKING AND USING THEREOF

CROSS-REFERENCE TO RELATED APPLICATIONS

This application claims the benefit of U.S. Patent Application Ser. No. 61/062,401, filed 24 Jan. 2008, U.S. Patent Application Ser. No. 61/062,545, filed 24 Jan. 2008, and U.S. Patent Application Ser. No. 61/142,780, filed 6 Jan. 2009, all of which are herein incorporated by reference in their entirety.

ACKNOWLEDGEMENT OF GOVERNMENT SUPPORT

Employees of Sandia National Laboratories made this invention. The government has certain rights in the invention.

BACKGROUND OF THE INVENTION

1. Field of the Invention

The present invention generally relates to methods for embedding micropores in microchannels and devices thereof using a single-level etching process and to tailoring the physical characteristics of these micropores for biological and chemical analysis.

2. Description of the Related Art

The concept of micro total analysis systems (microTAS) introduced for chemicals in the early 1990s by Manz et al. has been embraced by researchers in the emerging field of systems biology for studying the intra- and inter-cellular workings of a cell. See Manz et al. (1990) Sensors and Actuators B-Chemical 1:244-248, and Breslauer et al. (2006) Molecular Biosystems 2:97-112. These microfluidic platforms enable multiplexed studies at the single-cell level in a controlled microenvironment with the inherent advantages of fast reaction times, small reagent consumption, and parallelization.

The vast majority of these devices are focused on a single functionality or one basic operation. See El-Ali et al. (2006) Nature 442:403-411. Only a handful of truly integrated cell-based microfluidic platforms with multiple components have been reported. Examples include a high-density array with hundreds of individually addressable cell chambers; a device for single-cell manipulation, lysis, amino acid/protein labeling, and separation; and a microfluidic chip to continuously monitor secreted insulin from multiple independent islets of Langerhans. See Thorsen et al. (2002) Science 298:580-584; Wu et al. (2004) PNAS USA 101:12809-12813; Huang et al. (2007) Science 315:81-84; and Dishinger & Kennedy (2007) Anal. Chem. 79:947-954. The majority of these multiplexed platforms are fabricated from poly(dimethyl-siloxane) (PDMS) because microstructures such as valves, weirs, and micropores can be easily embedded within a network of microfluidic channels. See Duffy (1998) Anal Chem. 70:4974-4984; and Unger et al. (2000) Science 288:113-116; and Di Carlo et al. (2006) Anal. Chem. 78:4925-4930; and Seo et al. (2004) Applied Physics Letters 84:1973-1975.

Historically, silicon and glass have been the preferred substrate for the fabrication of microfluidic chips. See McCreedy (2000) Trac-Trends in Analytical Chemistry 19:396-401; and Ziaie et al. (2004) Advanced Drug Delivery Reviews, 56:145-172. Despite the wide academic acceptance of PDMS-based microfluidic chips, glass remains an attractive alternative for many biological applications because of its large optical transition range (180-2500 nm); high resistance to mechanical stress, heat, and chemicals; high electric isolation; absence of porosity; and high biocompatibility through its well-studied surface chemistry.

Of the three major glass etching techniques—mechanical, dry, and wet—the most common microfabrication method practiced is isotropic wet etching. Well characterized in the literature, this straight-forward fabrication method uses a photolithography mask to define features on the surface of the wafer. Sec Jacobson et al. (1995) Anal. Chem. 67:2059-2063; Madou, Fundamentals of Microfabrication, CRC Press, Boca Raton, Fla., 1997. Timed exposure to chemical etchants such as HF dissolves the Si—O—Si bonds in the glass isotropically, generating a D-shaped channel with a smooth surface and a constant depth. However, this technique is limited in that shallow structures (i.e. channels and weirs) are difficult to manufacture within larger channels without performing a multi-level wet etch or a combination of dry and wet etch—a costly and time-consuming operation because of the multiple masks and alignment steps needed between the different levels.

Therefore, a need exists for methods for making microstructures (e.g. micropores, ridges, etc.) within microfluidic channels for on-chip cell manipulation using single-step isotropic wet etch.

SUMMARY OF THE INVENTION

The present invention provides a method for forming a micropore between two isotropic wet etched features in a substrate which comprises single-level isotropic wet etching the two features using an etchant and a mask distance that is less than 2× a set etch depth. In some embodiments, the two features are two microchannels. In some embodiments, the micropore is a point-to-point micropore which is formed by an end of one microchannel intersecting with an end of the other microchannel. In some embodiments, the micropore is a point-to-edge micropore which is formed by an end of one microchannel intersecting with a side of the other microchannel. In some embodiments, the micropore is an edge-to-edge micropore which is formed by a side of one microchannel intersecting with a side of the other microchannel.

In some embodiments, the mask distance is $$g=\sqrt{4 \cdot d^2 - (2(h-b))^2}$$

wherein d is the set etch depth, h is the desired height of the micropore, and b is a calculated systematic error. In some embodiments, the mask distance is $g=\sqrt{4 \cdot d^2 - (w-b)^2}$ where the micropore is a point-to-point micropore, or $$g = d + \frac{1}{2}\sqrt{4 \cdot d^2 - (w-b)^2}$$

where the micropore is a point-to-edge micropore, wherein d is the set etch depth, w is the desired width of the micropore, and b is a calculated systematic error.

In some embodiments, the calculated systemic error is calculated by obtaining measured heights for a plurality of calibration micropores which were formed by single-level isotropic wet etching the features in the substrate with the etchant at the set etch depth and at a plurality of mask distances ranging from about 2× or less the set etch depth; and using nonlinear regression analysis to fit the measured heights to the following equation $$h_m = \frac{1}{2}\sqrt{4d^2 - g^2} + b$$

where $h_m$ is the measured height of the calibration micropore.

In some embodiments, where the micropore is the point-to-point micropore, the calculated systemic error is calculated by obtaining measured widths for a plurality of calibration micropores which were formed by single-level isotropic wet etching the features in the substrate with the etchant at the set etch depth and at a plurality of mask distances ranging from about 2× or less the set etch depth; and using nonlinear regression analysis to fit the measured widths to the following equation $$w_m = \sqrt{4 \cdot d^2 - g^2} + b$$

where $w_m$ is the measured width of the calibration micropore.

In some embodiments, where the micropore is the point-to-edge micropore, the calculated systemic error is calculated by obtaining measured widths for a plurality of calibration micropores which were formed by single-level isotropic wet etching the features in the substrate with the etchant at the set etch depth and at a plurality of mask distances ranging from about 2× or less the set etch depth; and using nonlinear regression analysis to fit the measured widths to the following equation $$w_m = 2\sqrt{(2d-g)g} + b$$

where $w_m$ is the measured width of the calibration micropore.

In some embodiments, the plurality of calibration micropores comprises about at least about 10 micropores, preferably about 10 to 30, more preferably about 15 to 20 calibration micropores.

In some embodiments, a micropore according to the present invention has a zero thickness or a near-zero thickness. In some embodiments, the width of a micropore according to the present invention is about two times the height of the micropore. In some embodiments, a micropore according to the present invention is less than about 7 μm in height.

In some embodiments, a cover is attached to a substrate wherein a micropore according to the present invention has been formed such that the cover forms a wall of the micropore, the features or both. In some embodiments, the cover comprises a micropore which is aligned over the micropore in the substrate to form a compound micropore having a top portion and a bottom portion. In some embodiments, the top portion and the bottom portion are symmetrical or asymmetrical. In some embodiments, the center of the top portion is centered over the center of the bottom portion or the center of the top portion is off-center over the center of the bottom portion.

In some embodiments, one or more steps of the method according to the present invention is conducted with a computer. For example, in some embodiments, the mask distance, the calculated systemic error, or both are calculated with a computer.

The present invention provides a micropore made by the methods disclosed herein. In some embodiments, the present invention provides a microfluidic device having a micropore made by the methods disclosed herein.

In some embodiments, a micropore as disclosed herein is used to concentrate particles in a fluid. In some embodiments, a micropore as disclosed herein is used as a hydrodynamic confinement trap. In some embodiments, a micropore as disclosed herein is used to encapsulate a particle in a picoliter droplet.

In some embodiments, a plurality of micropores as disclosed herein are used to fractionate a fluid sample using a plurality of microchannels which are interconnected by the micropores which are ordered by decreasing pore size along the direction of fluid flow. In some embodiments, the microchannels are parallel to each other. In some embodiments, the microchannels are in series.

In some embodiments, a micropore as disclosed herein is used to vertically focus a fluid or a particle. In some embodiments, vertical focusing of a fluid or particle using a micropore as disclosed herein is conducted in conjunction with planar focusing methods, such as hydrodynamic focusing, known in the art in order to provide 3D hydrodynamic focusing.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1A shows a top view of 30-μm-deep channels with overlapping corners. The negative image of the photomask is in white with a 56-μm mask distance. FIG. 1B is a cross-sectional view along main axis defined in FIG. 1A. FIG. 1C is angled view.

FIG. 2A is a 3D reconstruction from a stack of confocal micrographs taken using laser-scanning confocal fluorescence microscopy. FIG. 2B is a SEM micrograph angled at 40°.

FIG. 4A shows micropore width for point-to-point configuration at 25.03-μm and 29.78-μm etch depths and point-to-edge configuration at a 29.78-μm etch depth. FIG. 4B shows micropore depth for point-to-point configuration at a 25.03-μm and 29.78-μm etch depths.

FIGS. 5A-5G show various micropore designs for a 60-μm mask distance and a 30-μm-deep etched channel. FIGS. 5A-5E are micrographs of point-to-point designs. FIG. 5F is a point-to-edge design. FIG. 5G is an edge-to-edge design.

FIG. 6A shows a full circular micropore by aligning and bonding two identical semicircular micropore structures directly on top of each other. FIG. 6B shows a near-zero thickness horizontal slit at the intersection of two parallel D-shape channels. FIG. 6C shows a near-zero thickness slit with a variable height at the intersection of two D-shape channels separated by a variable distance. FIG. 6D shows a near-zero thickness slit that follows an arc at the intersection of two concentric arcs of a photolithographic mask.

FIGS. 7A-7G show an example of a continuous-flow cell concentrator, its characterization, and performance according to the present invention. FIG. 7A shows a micrograph comprising of 42 shunts connecting the sample (outer channel) to the waste (inner channel). Inset shows an SEM micrograph of one shunt with two micropores at its extremities (rotated). FIG. 7B shows that by applying pressure differentials $\Delta P=2$ psi, $\delta P=0.15$ psi, small fractions of tracer dye are withdrawn from the sample to the waste through successive shunts. FIG. 7D is a schematic of a flow circuit model for a concentrator, fluid reservoirs and connecting flow paths according to the present invention. FIGS. 7E-7F show the empirical determination of $R_i+R_o$ and $R_p$. FIG. 7E provides the experimental data for the ratios of the inlet and outlet pressure differential $\Delta P$ to the total flow rate $\Sigma Q$ for a wide range of operating conditions. FIG. 7F provides the experimental data for the ratios of the sample and waste pressure differential $\delta P$ to the transverse flow rate $\delta Q$ for a wide range of operating conditions. FIG. 7G is a graph of the predicted and measured concentration factors as a function of pressure differential $\delta P$ for 5 different total flow rates $\Sigma Q$.

FIGS. 8A-8C show an example of a micropore acting as a hydrodynamic trap for the immobilization of a single cell. FIG. 8A shows a single mouse macrophage cell trapped by a micropore imaged by a 40×0.60 NA objective. FIG. 8B shows a single mouse macrophage cell trapped by a micropore imaged by differential interference microscopy using a 60×1.42 NA oil-immersion objective. FIG. 8C shows the nuclear translocation of NF-κB in a macrophage cell trapped by micropores. The fluorescent micrograph on the left shows GFP-RelA located in the cytosol prior to activation (before LPS). The fluorescent micrograph on the right shows GFP-RelA located in the nucleus after a 30 min challenge (after LPS).

FIG. 9A shows the formation and breakoff of an aqueous droplet into a silicone oil stream at a micropore T-junction. FIG. 9B shows a stream of aqueous fluorescent droplets in mineral oil using a T-junction connected by a 20 µm tall pore. FIG. 9C shows laser-scanning confocal images of fixed, Alexa Fluor 488-labeled *E. coli* cells encapsulated on-chip in aqueous droplets generated at a micropore T-junction, and spotted onto a coverslip for imaging. The images are composites of transmitted light and fluorescence images acquired simultaneously with a 60×1.4 NA objective. Cell boundaries appear blurry due to Brownian motion during the laser-scanning time.

FIG. 10A shows finite element analysis modeling of hydrodynamic focusing at a micropore T-junction (cross-sectional view). Inset shows a micrograph of the micropore T-junction (planar view). FIG. 10B shows that without the micropore at the T-junction, the sample is not focused in the vertical axis (cross-sectional view). Inset shows a micrograph of the T-junction without the micropore (planar view).

DETAILED DESCRIPTION OF THE INVENTION

Figure 1A:
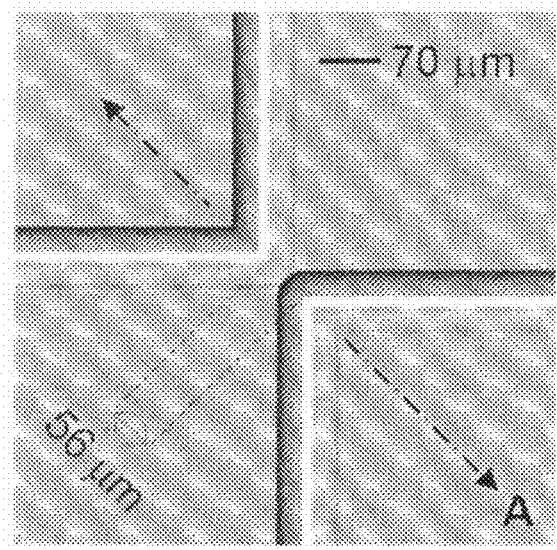
FIGS. 1A-1C show a CAD model of micropore fabrication in a point-to-point configuration.

The present invention relates to methods for embedding micropores in microchannels in substrates that wet etches isotropically using a single-step (also referred to herein as "single-level") etching process. In particular, the methods of the present invention control the overlap between two isotropic wet etch fronts to create a micropore having a zero thickness at the intersection of the isotropic wet etch fronts. As disclosed herein, the distance between features on the photolithographic mask (mask distance) can be controlled, to adjust the amount of overlap between the two etch fronts to create a micropore of a desired size at the intersection of the wet etch fronts.

Isotropic wet etching is a method known in the art for the uniform removal of materials from a substrate using a chemical etchant which etches the substrate in all directions when applied thereto. Although the prior art has employed single-level isotropic wet etching to create microstructures, such as basic weir microstructures, the prior methods do not teach or suggest how to obtain a micropore having a zero thickness and a desired size. See Sato et al. (2004) Lab on a Chip 4:570-575; Haes et al. (2006) Anal. Chem. 78:8412-8420; and Fu et al. (2008) Electrophoresis 29:1874-1880, which are herein incorporated by reference.

As provided herein, it was discovered that if two mask openings are placed at a distance of less than about 2× their etch depth apart, then the intersection of the resulting isotropic etching (overlapped isotropic wet etched fronts) will create an opening (e.g. micropore or slit) that has a zero thickness. As referred to herein, "zero thickness" means that the edge which defines an opening has no appreciable thickness. As referred to herein, "near-zero thickness" means the edge which defines an opening has a negligible or insignificant thickness. It should be noted that a two level etch cannot produce this feature as it will always have a finite thickness through the opening.

Thus, according to the present invention, the overlap of two etch fronts is controlled to create micropores of defined width and height. As provided herein, the measured micropore width and height are in good agreement with simple geometrical models, which can be used to precisely tailor the size of the micropore for different desired applications, e.g. continuous-flow concentration of particles, trapping of a single cell, and generation of picoliter-sized droplets as exemplified herein.

As used herein, "channel" refers to a structure wherein a fluid may flow. A channel may be a capillary, a conduit, a strip of hydrophilic pattern on an otherwise hydrophobic surface wherein aqueous fluids are confined, and the like. As used herein, "microfluidic" refers to a system or device having one or more fluidic channels, conduits or chambers that are generally fabricated at the millimeter to nanometer scale. Thus, the "microfluidic channels" or alternatively referred to herein as "microchannels" of the present invention generally have cross-sectional dimensions ranging from about 10 nm to about 1 mm.

As used herein, a "particle" may be natural or synthetic chemicals or biological entities. Chemicals and biological entities (biomolecules) include industrial polymers, powders, latexes, emulsions, colloids, environmental pollutants, pesticides, insecticides, drugs such as cocaine and antibiotics, magnetic particles, high-magnetic-permeability particles, metal ions, metal ion complexes, inorganic ions, inorganic ion complexes, organometallic compounds, metals including aluminum, arsenic, cadmium, chromium, selenium, cobalt, copper, lead, silver, nickel, and mercury, and the like, amino acids, peptides, proteins, glycoproteins, nucleotides, nucleic acid molecules, carbohydrates, lipids, lectins, cells, viruses, viral particles, bacteria, organelles, spores, protozoa, yeasts, molds, fungi, pollens, diatoms, toxins, biotoxins, hormones, steroids, immunoglobulins, antibodies, supermolecular assemblies, ligands, catalytic particles, zeolites, and the like, biological and chemical warfare agents, agents used in explosives, and the like.

As used herein, a "fluid" refers to a continuous substance that tends to flow and to conform to the outline of a container such as a liquid or a gas. Fluids include saliva, mucus, blood, plasma, urine, bile, breast milk, semen, water, liquid beverages, cooking oils, cleaning solvents, ionic fluids, air, and the like. Fluids can also exist in a thermodynamic state near the critical point, as in supercritical fluids.

The substrate used for the fabrication of the micropores according to the present invention can be any material, e.g. glass, oxide, nitride, aluminum, polysilicon, gold, plastics, and silicon, that is etched by a chemical isotropic etchant. For example, fused silica is an amorphous material that wet etches isotropically. A 10-μm-wide line on a photolithography mask with a 30-μm etch depth will result in about a 70-μm-wide, D-shaped channel. See Jacobson et al. (1995) Anal. Chem. 67:2059-2063; and Madou, Fundamentals of microfabrication, CRC Press, Boca Raton, Fla., 1997, which are herein incorporated by reference. As used herein, etch depth is the depth of an etched feature at its deepest etched point, i.e. the distance between the deepest etched point to the point directly above and at the surface of the substrate prior to etching.

Methods known in the art may be used to etch a given substrate to a desired or set etch depth with a given etchant. For example, to achieve a desired etch depth for a given substrate and a given etchant, the substrate is immersed in a recirculating bath containing the etchant for a period of time based on the etch rate of the given substrate for the given substrate such that the etch time is equal to the desired depth divided by the etch rate. Etch rates for various etchants and substrates are known in the art or can readily be determined using methods known in the art. See e.g. M. J. Madou, Fundamentals of microfabrication, CRC Press, Boca Raton, Fla., 1997, the internet having the following webpage: hypertext transfer protocol secure spf.stanford.edu/SNF/processes/process-modules/etching/wet-etching, and Williams et al. (2003) J of Microelectromechanical Systems 12(6):761-778, which are herein incorporated by reference. As is known in the art, the maximum etch depth possible is dependent on the given resist used as the mask, the given etchant and the given substrate. Thus, in preferred embodiments, the desired or set etch depth does not exceed the maximum etch depth possible for the resist, etchant and substrate to be employed. One skilled in the art may readily determine the maximum etch depth possible for a given resist, given etchant and given substrate using methods and knowledge known in the art.

Various methods for isotropic wet etching known in the art may be used in accordance with the present invention. For example, a double dip etch may be employed to accurately control the etch depth to that desired. The first dip is timed to produce about 75-85% of the desired etch depth, based on the expected etch rate. After the first dip, the substrate is removed from the recirculating bath and the actual etch depth obtained in the first dip is measured using a profilometer. Using the measured etch depth, the actual etch rate is refined (actual etch rate=measured etch depth during 1st dip/immersion time of 1st dip) to determine the immersion time for the second dip, as follows: Immersion time 2nd dip=(final depth−measured depth during 1st dip)/actual etch rate. The maximum etch depth possible is defined by the ability of the resist to withstand the etchant (for example: 35-40 μm maximum etch depth for fused silica).

Figure 1B:
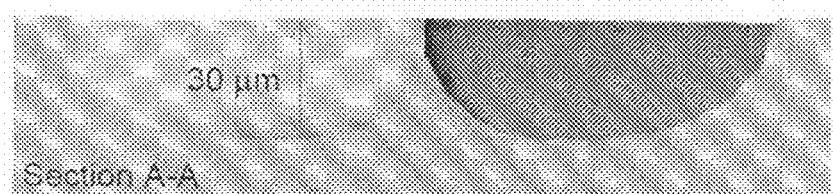
Figure 1C:
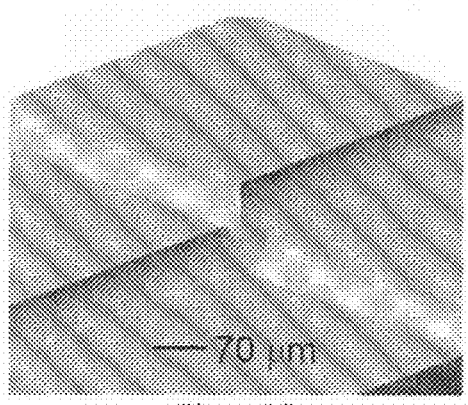
Figure 2A:
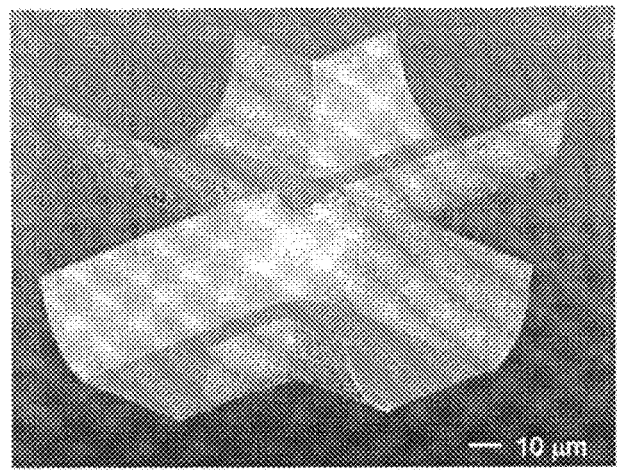
FIGS. 2A-2B are imaged micropores fabricated by overlapping isotropic wet-etch fronts.
Figure 2B:
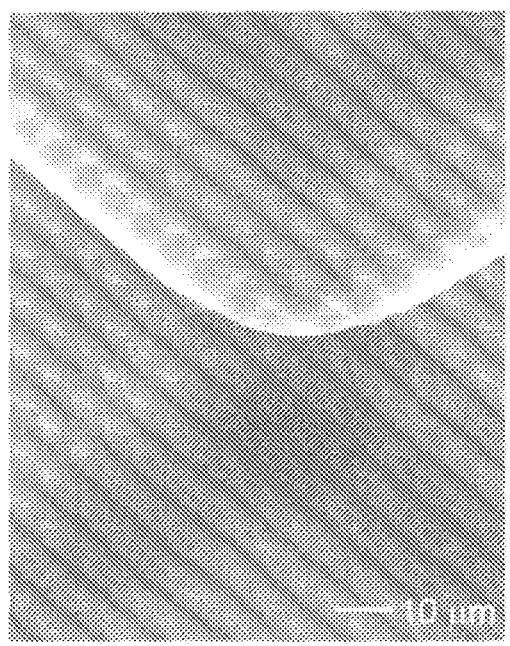

If mask features are separated from each other by a distance that is less than twice the etch depth, the isotropic wet etch will start to break through the channel sidewall near the top of the wafer to create a small opening where the two etched fronts first meet. Conceptually, two corners of a photolithographic mask that are separated by a distance of 56 μm will generate a zero-thickness semi-circular micropore at the intersection of two D-shape channels etched 30 μm deep. See FIGS. 1A-1C. The location of a fabricated micropore was imaged by laser-scanning confocal microscopy in a quartz microfluidic chip filled with a 100 μm solution of fluorescein. The 3D reconstruction of a stack of confocal images confirms the micropore location at the intersection of the two channel corners. See FIG. 2A. In reality, the shape of the micropore was semi-elliptical as shown by the angled SEM image of a 20-μm-wide and 6-μm-deep micropore. See FIG. 2B.

As provided herein, the fabrication of micropores within microfluidic channels may be tailored to give a desired size using a predictive geometrical model based on a hemispherical etch front and isotropic wet etching, preferably single-level isotropic wet etching. The predictive geometrical model disclosed herein characterizes the dependence of the micropore width and height to the distance separating the mask features. As used herein, "mask distance" refers to the minimum distance separating two mask features, i.e. the shortest distance between the two mask features.

Although only two configurations on the photolithographic mask, point-to-point and point-to-edge, are exemplified herein, edge-to-edge, is also contemplated herein. In a point-to-point (p2p) configuration, as exemplified in FIG. 5D, the mask distance is defined as the minimum distance between the tips of two opposing triangles; whereas, in point-to-edge (p2e) configuration, as exemplified in FIG. 5F, the mask distance is defined as the minimum distance between the tip of a triangle and a straight edge. In edge-to-edge, the mask distance is defined as the minimum distance between two opposing edges, as exemplified in FIG. 5G.

From trigonometry and the intersection of standard geometrical shapes, the micropore width, $w_{p2p}$, for the point-to-point configuration is given by Equation 1.1a:

$$w_{p2p} = \sqrt{4d_{p2p}^2 - g_{p2p}^2} + b_{p2p} \qquad \text{Eq. 1.1a}$$

where $d_{p2p}$ is defined as the etch depth, g the mask distance, and $b_{p2p}$ a systematic error.

Figure 3:
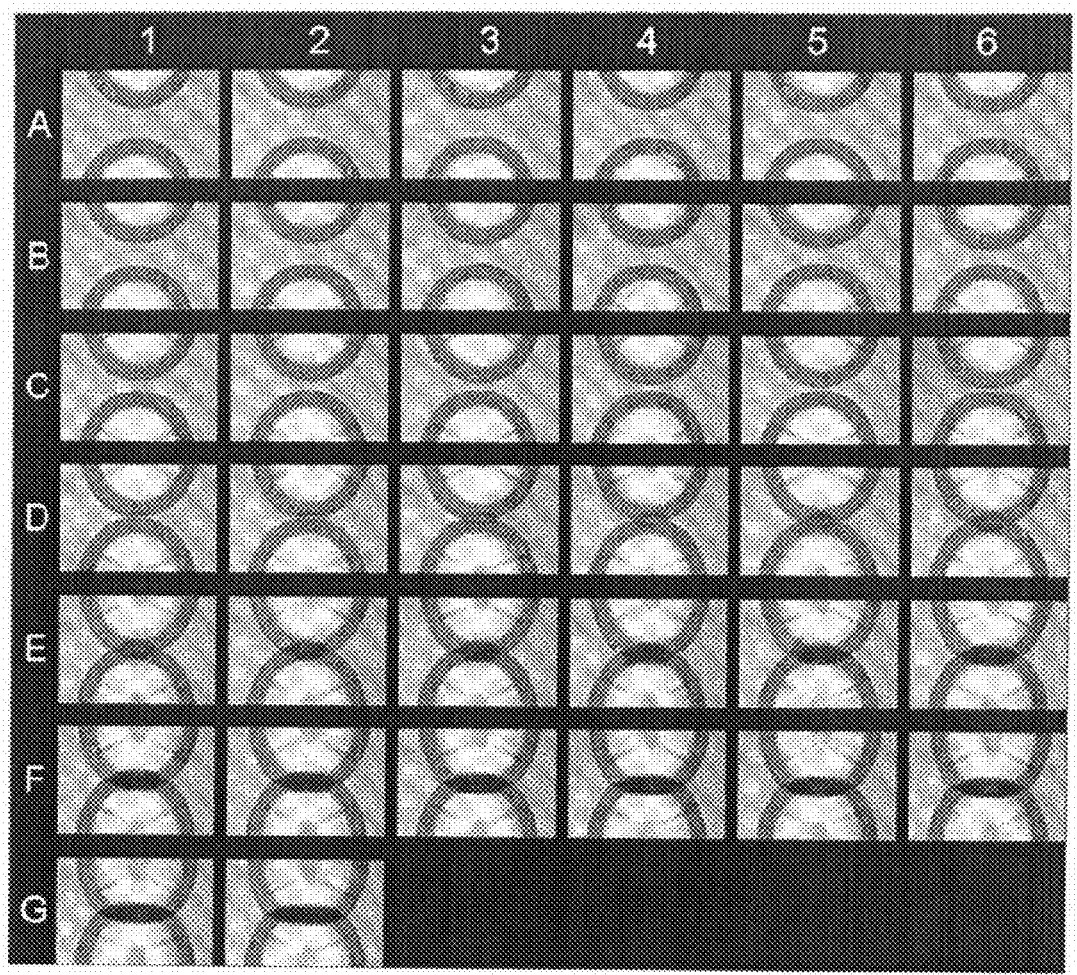
FIG. 3 is a set of 38 micrographs of channels in a point-to-point configuration etched at a set etch depth of 25 μm with mask distances decreasing incrementally by 1 μm from 67 μm (micrograph at col. 1, row A) to 30 μm (micrograph at col. 2, row G).

To determine the value of the systematic error $b_{p2p}$, Equation 1.1a was calibrated against 14 calibration micropores (micropores used for determining the value of the systemic error) etched 25.03 μm deep with mask distances changing by increments of 1 μm starting from 50 μm and ending with 37 μm as shown in Table 1. The micrographs provided in FIG. 3 show contact between the etched fronts at a mask distance of about 50 μm, which is the theoretical expected value (twice the etch depth). The width of each calibration micropore was measured using high resolution brightfield microscopy and methods known in the art. The measured calibration micropore width was then plotted against the mask distance as exemplified in FIG. 4A. Nonlinear regression analysis and methods known in the arts, such as an ordinary and weighted least-squares, to fit Equation 1.1a to the measured calibration micropore widths to recover the systemic error, $b_{p2p}$. In particular, a weighted least-squares Marquardt-Levenberg algorithm was used to fit Equation 1.1a to the measured calibration micropore widths to recover a systematic error b=3.4 μm. The recovered etch depth from the same nonlinear regression analysis ($d_{p2p}$=25.0 μm) was in good agreement with the profilometer-measured value (25.01 μm, Table 1) and confirms the validity of the calibration.

Equation 1.1a can be rearranged to be $$g_{p2p} = \sqrt{4d_{p2p}^2 - (w_{p2p} - b_{p2p})^2} \qquad \text{Eq. 1.1b}$$

Equation 1.1b can be used to determine the mask distance, $g_{p2p}$, which will result in a micropore having a desired width for a point-to-point configuration for a given substrate, a given etchant and a set etch depth. In some embodiments, the set etch depth does not exceed the maximum etch depth possible for the given substrate, the given etchant and the resist employed. In some embodiments, the set etch depth is less than the maximum etch depth possible for the given substrate, the given etchant and the resist employed. The values for the mask distance, $g_{p2p}$, range from zero up to twice the etch depth.

Thus, the present invention provides a method for obtaining a micropore having a desired width, which comprises isotropic wet etching two features, e.g. microchannels, in a point-to-point configuration in a given substrate at a set etch depth using a mask distance of $g_{p2p}$. For example, a micropore width, $w_{p2p}$, of 20 µm is desired between two isotropic wet etched features, e.g. microchannels, in a point-to-point configuration and having an etch depth, $d_{p2p}$, of 25.0 µm. The systemic error, $b_{p2p}$, is determined by calibrating Equation 1.1a against at least 10, preferably about 10 to about 30, more preferably about 15 to about 20 calibration micropores formed two overlapping isotropic wet etched features which are etched at the set etch depth with a plurality of mask distances, e.g. mask distances changing by increments of 1 µm starting from 2× to about 1.5× the set etch depth. The features are etched to the set etch depth as described above and using methods known in the art. The width of each calibration micropore is measured using methods known in the art. The measured calibration micropore widths are then plotted against the mask distances and nonlinear regression analysis and methods known in the arts are used to fit Equation 1.1a to the measured calibration micropore widths to recover the systemic error, $b_{p2p}$. The recovered systemic error, the desired micropore width, and the set etch depth are then used to calculate the mask distance which will result in the desired micropore width.

For example, solving Equation 1.1b for a given substrate and a given etchant, where the desired micropore width, $w_{p2p}$, is 20 µm, the set etch depth is 25 µm, and the systemic error, $b_{p2p}$, is 3.4 µm gives a mask distance, $g_{p2p}$, as follows:

$$\sqrt{4 \cdot 25^2 - (20 - 3.4)^2} = 47.2 \text{ µm}$$

Thus, for the given substrate and the given etchant one would place the mask features 47.2 µm apart and etch to the set etch depth, $d_{p2p}$, of 25 µm in order to obtain a micropore having a width of about 20 µm. Similarly, where the desired micropore width, $w_{p2p}$, is 10 µm, the set etch depth is 28 µm, and the systemic error, $b_{p2p}$, is 2.1 µm, the calculated mask distance, $g_{p2p}$, is 55.4 µm.

In the point-to-edge configuration, the micropore width, $w_{p2e}$, is given by Equation 1.2a:

$$w_{p2e} = 2\sqrt{(2d_{p2e} - g_{p2e})g_{p2e}} + b_{p2e} \qquad \text{Eq. 1.2a}$$

To determine the value of the systematic error, $b_{p2e}$, Equation 1.2a was calibrated against 13 calibration micropores etched 29.78 µm deep with mask distances changing by increments of 1 µm starting from 62 µm and ending with 50 µm as exemplified in Table 1. The width of each calibration micropore was measured using high resolution brightfield microscopy and methods known in the art. The measured calibration micropore width was then plotted against the mask distance as exemplified in FIG. 4A. Nonlinear regression analysis and methods known in the arts, such as an ordinary and weighted least-squares, to fit Equation 1.2a to the measured calibration micropore widths to recover the systemic error, $b_{p2e}$. In particular, a weighted least-squares Marquardt-Levenberg algorithm was used to fit Equation 1.2a to the measured calibration micropore widths to recover a systematic error b=2.3 µm. The recovered etch depth from the same nonlinear regression analysis ($d_{p2e}$=31.7 µm) was in good agreement with the profilometer-measured value (29.78 µm, Table 1) and confirms the validity of the calibration.

Equation 1.2a can be rearranged to be $$g_{p2e} = d_{p2e} + \frac{1}{2}\sqrt{4d_{p2e}^2 - (w_{p2e} - b_{p2e})^2} \qquad \text{Eq. 1.2b}$$

Equation 1.2b can be used to determine the mask distance, $g_{p2e}$, which will result in a micropore having a desired width for a point-to-edge configuration for a given substrate, a given etchant and a set etch depth. In some embodiments, the set etch depth does not exceed the maximum etch depth possible for the given substrate, the given etchant and the resist employed. In some embodiments, the set etch depth is less than the maximum etch depth possible for the given substrate, the given etchant and the resist employed. The values for the mask distance, $g_{p2e}$, range from zero up to twice the etch depth.

Thus, the present invention provides a method for obtaining a micropore having a desired width, which comprises isotropic wet etching two features, e.g. microchannels, in a point-to-edge configuration in a given substrate at a set etch depth using a mask distance of $g_{p2e}$. For example, a micropore width, $w_{p2e}$, of 20 µm is desired between two isotropic wet etched features, e.g. microchannels, in a point-to-point configuration and having an etch depth, $d_{p2e}$, of 31.7 µm. The systemic error, $b_{p2e}$, is determined by calibrating Equation 1.2a against at least 10, preferably about 10 to about 30, more preferably about 15 to about 20 calibration micropore formed two overlapping isotropic wet etched features which are etched at the set etch depth with various mask distances, e.g. mask distances changing by increments of 1 µm starting from 2× to about 1.5× the set etch depth. The features are etched to the set etch depth as described above and using methods known in the art. The width of each calibration micropore is measured using methods known in the art. The measured calibration micropore widths are then plotted against the mask distances and nonlinear regression analysis and methods known in the arts are used to fit Equation 1.2a to the measured calibration micropore widths to recover the systemic error, $b_{p2e}$. The recovered systemic error, the desired micropore width, and the set etch depth are then used to calculate the mask distance which will result in the desired micropore width.

For example, solving Equation 1.2b for a given substrate and a given etchant, where the desired micropore width, $w_{p2e}$, is 20 µm, the set etch depth is 31.7 µm, and the systemic error, $b_{p2e}$, is 2.3 µm gives a mask distance, $g_{p2e}$, as follows:

$$31.7 + \frac{1}{2}\sqrt{4 \cdot 31.7^2 - (20 - 2.3)^2} = 62.1 \text{ µm}$$

Thus, for the given substrate and the given etchant one would place the mask features 62.1 µm apart and etch to the set etch depth, $d_{p2e}$, of 31.7 µm in order to obtain a micropore having a width of about 20 µm. Similarly, where the desired micropore width, $w_{p2e}$, is 10 µm, the set etch depth is 28 µm, and the systemic error, $b_{p2e}$, is 2.1 µm, the calculated mask distance, $g_{p2e}$, is 55.7 µm.

For both a point-to-point and a point-to-edge configuration, the micropore height (depth), h, is given by Equation 1.3a:

$$h = \frac{1}{2}\sqrt{4d^2 - g^2} + b \qquad \text{Eq. 1.3a}$$

To determine the value of the systemic error, b, Equation 1.3a was calibrated against 11 calibration micropores etched 29.78 μm deep with mask distances changing by increments of 1 μm starting from 60 μm and ending with 50 μm as exemplified in Table 2. The height of each calibration micropore was measured using an automated microscope stage with closed-loop DC servo control of the vertical axis for precise and highly repeatable focusing and methods known in the art. The measured calibration micropore height was then plotted against the mask distance as exemplified in FIG. 4B. Nonlinear regression analysis and methods known in the arts, such as an ordinary and weighted least-squares, to fit Equation 1.3a to the measured calibration micropore heights to recover the systemic error, b. In particular, a weighted least-squares Marquardt-Levenberg algorithm was used to fit Equation 1.3a to the measured calibration micropore widths to recover a systematic error b=−3.6 μm. The recovered etch depth from the same nonlinear regression analysis (d=30.5 μm) was in good agreement with the profilometer-measured value (29.78 μm, Table 2) and confirms the validity of the calibration.

Equation 1.3a can be rearranged to be $$g = \sqrt{4d^2 - [2(h-b)]^2} \qquad \text{Eq. 1.3b}$$

Equation 1.3b can be used to determine the mask distance, g, which will result in a micropore having a desired height for either a point-to-point or a point-to-edge configuration for a given substrate, a given etchant and a set etch depth. In some embodiments, the set etch depth does not exceed the maximum etch depth possible for the given substrate, the given etchant and the resist employed. In some embodiments, the set etch depth is less than the maximum etch depth possible for the given substrate, the given etchant and the resist employed. The values for the mask distance, g, range from zero up to twice the etch depth.

Thus, the present invention provides a method for obtaining a micropore having a desired height, which comprises isotropic wet etching two features, e.g. microchannels in a given substrate at a set etch depth using a mask distance of $g_{p2e}$. For example, a micropore height, h, of 10 μm is desired between two isotropic wet etched features, e.g. microchannels, and having an etch depth, d, of 30.5 μm. The systemic error, b, is determined by calibrating Equation 1.3a against at least 10, preferably about 10 to about 30, more preferably about 15 to about 20 calibration micropores formed two overlapping isotropic wet etched features which are etched at the set etch depth with various mask distances, e.g. changing by increments of 1 μm starting from 2× to about 1.5× the set etch depth. The features are etched to the set etch depth as described above and using methods known in the art. The height of each calibration micropore is measured using methods known in the art. The measured calibration micropore heights are then plotted against the mask distances and nonlinear regression analysis and methods known in the arts are used to fit Equation 1.3a to the measured calibration micropore heights to recover the systemic error, b. The recovered systemic error, the desired micropore height, and the set etch depth are then used to calculate the mask distance which will result in the desired micropore height.

For example, solving Equation 1.3b for a given substrate and a given etchant, where the desired micropore height, h, is 10 μm, the set etch depth is 30.5 μm, and the systemic error, b, is −3.6 μm gives a mask distance, g, as follows:

$$\sqrt{4 \cdot 30.5^2 - [2*(10-(-3.6))]^2} = 54.6 \text{ μm}$$

Thus, for the given substrate and the given etchant one would place the mask features 54.6 μm apart and etch to the set etch depth, d, of 30.5 μm in order to obtain a micropore having a height of about 10 μm. Similarly, where the desired micropore height, h, is 5 μm, the set etch depth is 20 μm, and the systemic error, h, is −2.1 μm, the calculated mask distance, g, is 37.4 μm.

Figure 4A:
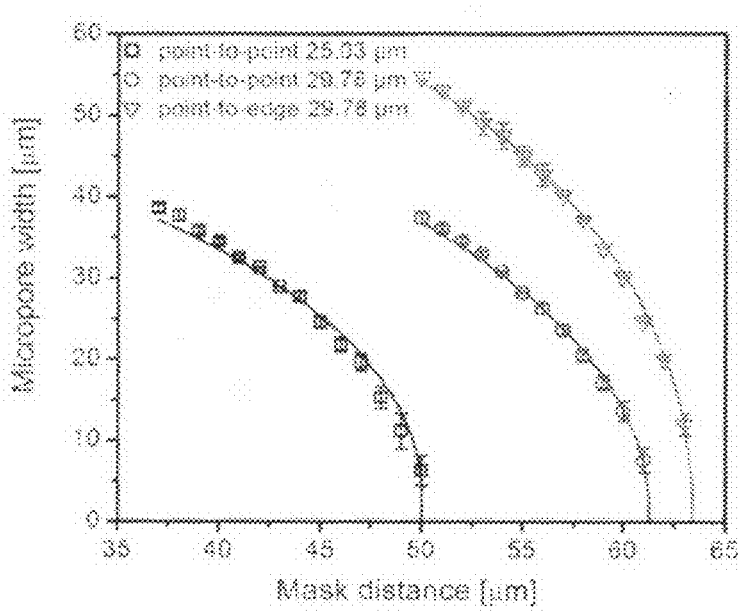
FIGS. 4A-4B show micropore width and depth as a function of mask distance for two configurations and etch depths.

The following Table 1 provides the mask distances, experimental micropore widths and theoretical micropore widths as provided in FIG. 4A:

TABLE 1

| Mask Distance μm | Experimental width μm | Theoretical width μm |
|---|---|---|
| point-to-point 25.03 μm | | |
| 37 | 38.6 ± 0.5 | 37.0 |
| 38 | 37.7 ± 0.7 | 35.9 |
| 39 | 35.8 ± 0.6 | 34.7 |
| 40 | 34.5 ± 0.4 | 33.4 |
| 41 | 32.5 ± 0.3 | 32.0 |
| 42 | 31.3 ± 0.1 | 30.5 |
| 43 | 29.0 ± 0.1 | 28.9 |
| 44 | 27.8 ± 0.6 | 27.1 |
| 45 | 24.6 ± 0.7 | 25.2 |
| 46 | 21.8 ± 0.9 | 23.0 |
| 47 | 19.7 ± 1.0 | 20.5 |
| 48 | 15.3 ± 1.4 | 17.4 |
| 49 | 11.2 ± 2.2 | 13.3 |
| 50 | 6.3 ± 1.9 | 3.4 |
| point-to-point 29.78 μm | | |
| 50 | 37.4 ± 0.7 | 36.7 |
| 51 | 36.0 ± 0.6 | 35.2 |
| 52 | 34.6 ± 0.4 | 33.7 |
| 53 | 33.0 ± 0.3 | 32.0 |
| 54 | 30.8 ± 0.1 | 30.2 |
| 55 | 28.2 ± 0.1 | 28.2 |
| 56 | 26.3 ± 0.6 | 26.1 |
| 57 | 23.7 ± 0.7 | 23.7 |
| 58 | 20.5 ± 0.8 | 20.9 |
| 59 | 17.2 ± 0.9 | 17.7 |
| 60 | 13.6 ± 1.2 | 13.5 |
| point-to-edge 29.78 μm | | |
| 50 | 54.7 ± 0.5 | 54.1 |
| 51 | 53.0 ± 0.5 | 52.6 |
| 52 | 51.2 ± 0.6 | 51.0 |
| 53 | 49.0 ± 1.4 | 49.3 |
| 54 | 47.5 ± 1.6 | 47.4 |
| 55 | 45.0 ± 1.2 | 45.3 |
| 56 | 42.6 ± 1.3 | 43.0 |
| 57 | 40.2 ± 0.0 | 40.5 |
| 58 | 37.1 ± 0.3 | 37.7 |
| 59 | 33.6 ± 0.0 | 34.5 |
| 60 | 30.1 ± 0.1 | 30.9 |
| 61 | 24.7 ± 0.0 | 26.5 |
| 62 | 20.1 ± 0.3 | 20.9 |

Figure 4B:
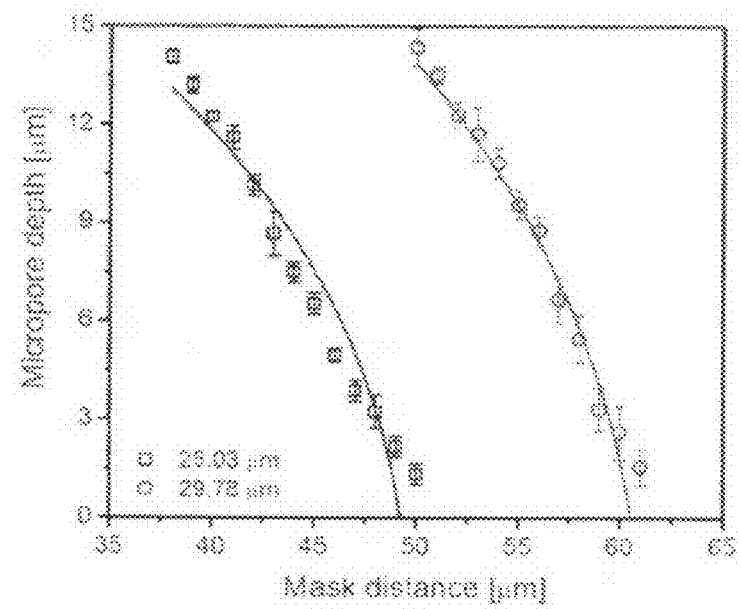

Table 2 provides the mask distances, experimental micropore heights and theoretical micropore heights as provided in FIG. 4B:

TABLE 2

| Mask Distance μm | Experimental Height μm | Theoretical Height μm |
|---|---|---|
| point-to-point 25.03 μm | | |
| 38 | 14.1 ± 0.2 | 13.8 |
| 39 | 13.2 ± 0.3 | 13.2 |

TABLE 2-continued

| Mask Distance μm | Experimental Height μm | Theoretical Height μm |
|---|---|---|
| 40 | 12.2 ± 0.2 | 12.5 |
| 41 | 11.6 ± 0.4 | 11.8 |
| 42 | 10.1 ± 0.3 | 11.1 |
| 43 | 8.7 ± 0.7 | 10.3 |
| 44 | 7.5 ± 0.3 | 9.4 |
| 45 | 6.5 ± 0.3 | 8.4 |
| 46 | 5.0 ± 0.2 | 7.2 |
| 47 | 3.9 ± 0.3 | 5.9 |
| 48 | 3.2 ± 0.5 | 4.3 |
| 49 | 2.2 ± 0.3 | 2.1 |
| 50 | 1.3 ± 0.3 | N/A |
| point-to-point 29.78 μm | | |
| 50 | 14.4 ± 0.6 | 13.9 |
| 51 | 13.5 ± 0.3 | 13.1 |
| 52 | 12.3 ± 0.4 | 12.3 |
| 53 | 11.7 ± 0.8 | 11.5 |
| 54 | 10.8 ± 0.5 | 10.6 |
| 55 | 9.6 ± 0.4 | 9.6 |
| 56 | 8.8 ± 0.5 | 8.5 |
| 57 | 6.6 ± 0.7 | 7.3 |
| 58 | 5.5 ± 0.7 | 5.8 |
| 59 | 3.3 ± 0.7 | 4.1 |
| 60 | 2.6 ± 0.8 | 1.9 |

As shown in FIG. 4A, the relationship between micropore width and mask distance is nonlinear. For the micropore height measurement, the range of mask distance probed is small and could be misconstrued as a linear function. See FIG. 4B. When the mask distance is extrapolated to zero using Equation 1.3a, the predicted micropore height is similar to the measured etch depth (within about 10%), which is not the case for a linear equation (over about 200%). The range of mask distance probed in FIG. 4B is biased towards the highly sloped part of Equation 1.3a.

Additionally, the misfit between theory and experiment has its greatest deviation for shallow micropores (about <4 μm), where the width-to-height ratio is greater than 4. However, as the micropore becomes larger, there is a clear trend for this ratio to approach the theoretical value of a semicircle where w/h=2. It is believe that the breakdown between theory and experiment for these shallow micropores is a consequence of mask lift-off undercutting the wafer. Overall, the parameters determined for different geometrical models or at different etch depths are in good agreement with the measured values, demonstrating the validity of geometrical models according to the present invention to predict the width and height of micropores fabricated by overlapping isotropic wet-etch fronts.

Table 3 below summarizes the recovered width and depth (micropore height) fitting parameters for each configuration with its corresponding chi-squared value.

TABLE 3

Summary of fitting results for measured values in FIGS. 4A and 4B.

| | micropore width | | | micropore depth | | |
|---|---|---|---|---|---|---|
| | d [μm] | b [μm] | $X^2_{red}$ | d [μm] | b [μm] | $X^2_{red}$ |
| point-to-edge (29.78 μm) | 31.7 | 2.3 | 0.05 | — | — | — |
| point-to-point (29.78 μm) | 30.6 | 1.4 | 0.08 | 30.5 | −3.6 | 0.28 |
| point-to-point (25.03 μm) | 25.0 | 3.4 | 1.9 | 24.9 | −2.3 | 0.36 |

Figure 5A:
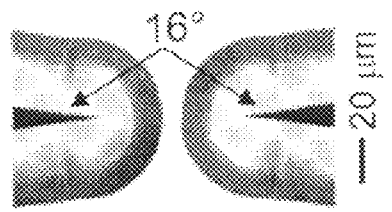
Figure 5B:
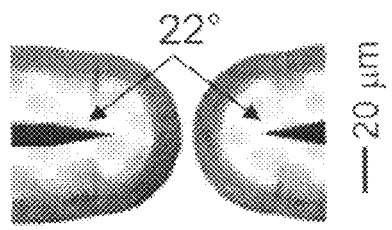
Figure 5C:
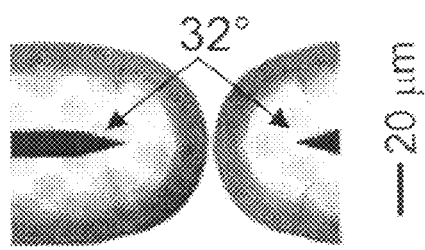
Figure 5D:
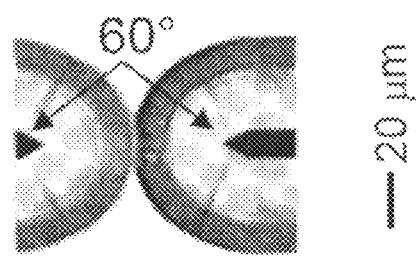
Figure 5E:
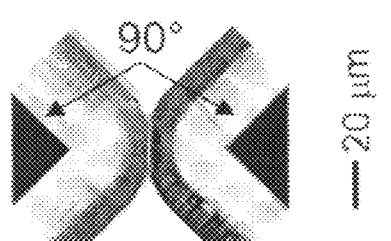

In addition to the geometrical equations discussed above, the potential sources of systematic error from the photolithographic mask or from inadequate reproducibility were investigated. A series of 30-μm-deep channels separated from each other by a 60-μm mask distance with different inclusive angles (16°-16°, 22°-22°, 32°-32°, 60°-60°, 90°-90°, 60°-180°, and 180°-180°) were imaged using brightfield microscopy. See FIG. 5A-5G. Despite a constant 60-μm mask distance, the resulting overlap between the channels was significantly different from each other. For example, as shown in FIG. 5A, for a 16°-16° configuration, no overlap was observed; whereas, as shown in FIG. 5E, a micropore was formed for a 90°-90° configuration.

This discrepancy is a direct result of limited resolution in the photolithographic mask. For sharp angles, such as a 16° angle, the tip of the triangle was in reality filleted by the laser scribe during the manufacturing of the mask, thereby increasing the effective mask distance. As the total angle increases, the effective mask distance becomes closer to the design mask distance thus increasing the extent of the overlap between the two etch fronts. Thus, although mask features having sharp angles (about <60°) can be used to create micropores according to the present invention, such features are not preferred as they introduce additional sources of error due to the limited resolution of the photolithographic mask.

As disclosed herein, the reproducibility of the micropores made according to the present invention was assessed within the same chip, between wafers processed simultaneously, and between wafers processed by different masks. All chips were custom-fabricated by Caliper Life Sciences (Mountain View, Calif.) using a standard recipe known in the art based on conventional photolithographic and wet-etch protocols described previously. See Throckmorton et al. (2002) Anal. Chem. 74:784-789, which is herein incorporated by reference. In all cases, the maximum variation in the micropore widths was about 2 μm or less. For instance, the average width for 11 micropores on the same chip was 18.6±1.2 μm. Therefore, the present invention provides reproducible methods of fabricating micropores having a desired size.

Figure 6A:
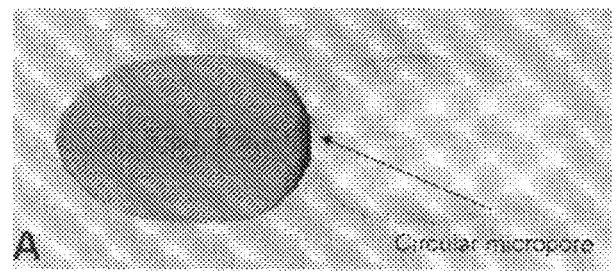
FIGS. 6A-6D show alternate configurations for embedding micropores and slits into channels.

As exemplified herein, micropores having semicircular or semi-elliptical profiles were created by etching a micropore in a base wafer and bonding the base wafer to an unetched cover wafer using methods known in the art. Nevertheless, according to the present invention full circular micropore profiles may be created by aligning and bonding two identical semicircular micropore structures directly on top of each other. See FIG. 6A.

Figure 6B:
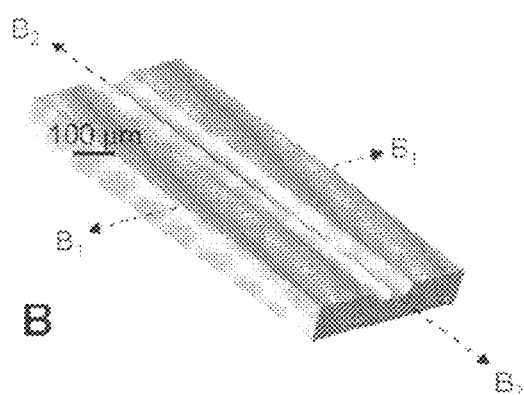
Figure 6B:
Figure 6B:
Figure 6C:
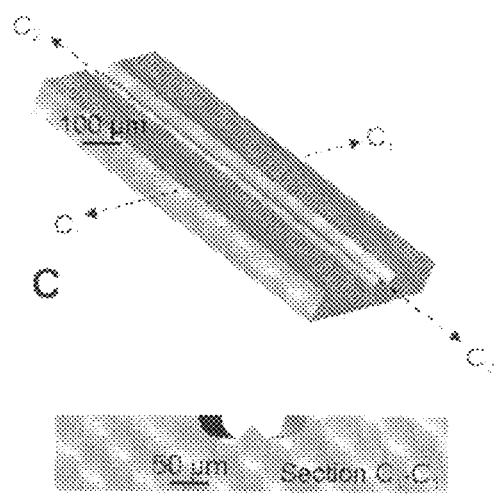
Figure 6C:
Figure 6D:
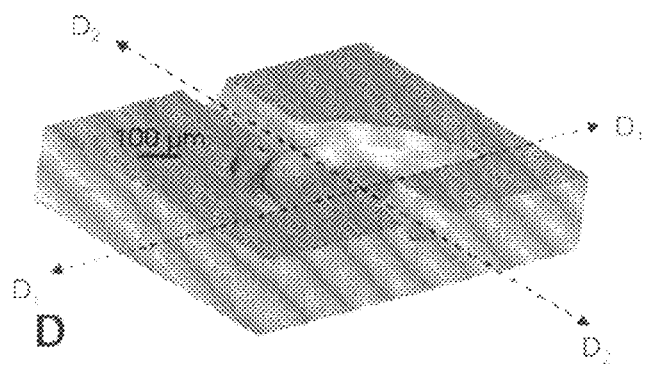
Figure 6D:
Figure 6D:
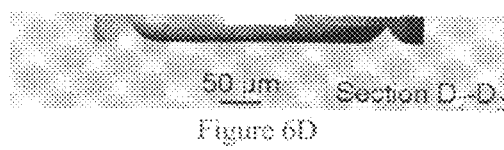

Additionally, in some embodiments, micropores of two different profiles can be aligned and bonded together to form different symmetries and different sizes. For example, using the edge-to-edge mask configuration, two overlapping fronts can be used to create an extended micropore or near-zero thickness horizontal slit near the top portion of the microchannel. Conceptually, two parallel edges of a photolithographic mask that are separated by a distance of 56 μm will generate a zero thickness (or near-zero thickness) horizontal slit at the intersection of two parallel D-shape channels etched 30 μm deep. See FIG. 6B. The width dimension is determined by and equal to the distance of overlap by the two fronts. The height of the horizontal slit is controlled by the mask distance, similar to pore-to-pore and pore-to-edge configuration. The width of the two D-shape channels can be similar or different. In addition, there is no limit to the width of the horizontal slit. As an alternative configuration, two edges of a photolithographic mask that are separated by a variable distance will generate a zero thickness (or near-zero thickness) slit with a variable height at the intersection of two D-shape channels. See FIG. 6C. The rate of change in the height of the slit can be smooth or incremental with discrete steps. Additionally, two concentric arcs of a photolithographic mask that are separated by a distance will generate a zero thickness (or near-zero thickness) slit that follows an arc instead of a straight line. See FIG. 6D.

The following examples are intended to illustrate but not to limit the invention.

Applications Using Micropores

The micropores made according to the present invention allow novel microfluidic processing and analysis on a substrate capable of being isotropically wet etched, such as a fused-silica chip. For example, the micropores of the present invention can be created and used as (1) discrete and continuous pores in a continuous-flow particle concentration device; (2) hydrodynamic traps to immobilize individual and multiple particles by hydrodynamic confinement; (3) orifices in T-junctions to generate aqueous picoliter-sized droplets in a immiscible carrier liquid; and the like.

Example 1 disclosed below shows how particles were continuously concentrated by successively removing a carrier fluid through a series of 44 discrete micropores (shunts) units between two congruent legs using pressure differentials. Theoretical values for the concentration factor determined by a flow circuit model in conjunction with finite volume modeling are experimentally validated. Example 2 provided below shows how macrophage cells were individually trapped in 40-μm-wide, 17-μm-deep micropores by hydrodynamic confinement. The nuclear translocation of transcription factor NF-kB upon lipopolysaccharide stimulation was then imaged by fluorescence microscopy. Example 3 disclosed below shows how individual E. coli cells were encapsulated in aqueous picoliter-sized droplets in an oil stream which were generated from a 50-μm-wide, 18-μm-deep micropore T-junction.

Chip Design and Fabrication

The chrome/quartz photomask (F62CQ6120; Photo-Sciences, Torrance, Calif.) for the microfluidic chips was designed in L-Edit layout editor (Tanner Research, Inc. Monrovia, Calif. using methods known in the art. The chips were fabricated using wet-etch and photolithographic methods known in the art. See Throckmorton et al. (2002) Anal. Chem. 74:784-789, which is herein incorporated by reference. Microchannels were isotropically etched in 0.70-mm-thick fused-silica base wafers. The final etch depth was measured across the wafer using a Tencor Alpha-Step profilometer (KLA-Tencor, Inc. Milpitas, Calif.) calibrated on a daily basis. Fluid access holes (500-μm diameter) were ultrasonically drilled into a cover wafer before being visually aligned and thermally bonded to the base wafer. The combined wafers were then diced with a wafer saw into individual 22.6×37.2 mm chips. To be compatible with large numerical aperture (NA) objective (≥1.4), the base wafer was polished to a final thickness of about 170 μm using a lapping-polishing process (GM Associates, Inc. Oakland, Calif.). The removal of about 530 μm of material from the base wafer left low levels of subsurface damages (commercial grade finish 80/50 scratch/dig), with a surface roughness of about 2 micro-inch. Prior to each use, the channels were coated with a solution having 4% bovine serum albumin to prevent particle or cell adhesion to the walls.

Chip Packaging

A custom-made Delrin manifold with integrated O-ring seals provides the interface between the microfluidic chip and fluid reservoirs. Fluid was delivered to each port of the manifold through 1/32" O.D. 0.005" I.D. PEEK tubing (1576; Upchurch Scientific, Oak Harbor, Wash.) and swaged in place with 1/32" TubeTite fittings (Labsmith, Livermore, Calif.). Screw-cap microcentrifuge tubes (2.0 ml—89004-302; VWR, West Chester, Pa.) fitted with custom-machined caps served as fluid reservoirs. The caps have two ports to allow the delivery of $N_2$ gas to pressurize the headspace in the vial and push the fluid through a PEEK tube placed below the liquid level into the chip. All fluid reservoirs were pressurized by individual electronic pressure control units (VSO-EP; Parker, Cleveland, Ohio) to ensure precise control of pressure drops across the microfluidic chip. To maintain a temperature of 37° C. in the chip, two 35 W low inductance resistors (TCH35P4R70JE; Ohmite Mfg. Rolling Medadow, Ill.) and a resistive thermal device sensor (RTD-830; Omega Engineering Stamford, Conn.) were mounted to the compression frame with common heat-sink grease and powered by a temperature controller (CN132-12V; Omega Engineering Stamford, Conn.). Flow rates were measured by Nano Flow sensors (N-565; UpChurch Scientific Oak Harbor, Wash.) calibrated against a syringe pump at room temperature prior to use. When measuring flow rates on a concentrator, the sensor readings and fluidic resistance were matched by using equal length precut PEEK tubing and positioning the outlet reservoirs at equal height. Flows for droplet generation were driven either by pressure controllers or by syringe pumps (NE-500; New Era, Wantagh, N.Y.). When pressure controllers were used, upstream pressures were typically about 10 psi for the oil stream, with the aqueous pressure adjusted between about 5 to about 8 psi. This configuration resulted in about a 1 μl/min oil flow rate, with generation of droplets from about 20 to about 80 Hz, and an aqueous/oil volumetric ratio between about 1/5 to about 1/20. When syringe pumps were used, oil flow rates were typically about 1 to about 3 μl/min, and aqueous flow rates were about 0.2 to about 0.6 μl/min.

Micropore Metrology

Three microscopy techniques were used to characterize the micropores: laser-scanning confocal fluorescence microscopy, field-emission scanning electron microscopy (FESEM), and bright-field microscopy. The micropore imaged by laser-scanning confocal fluorescence microscopy (MRC1024ES; Biorad, Hercules, Calif.), had a 100 μM solution of fluorescein flowing continuously throughout the chip during the scan to avoid photobleaching. Each confocal image was taken by a 60×1.4 NA oil-immersion objective (Nikon, Technical Instruments, San Francisco, Calif.). Three-dimensional reconstruction using 3D Doctor software (Able, Lexington, Mass.) was used for acquiring the sequential 0.5-μm-thick confocal images through a 30-μm-thick section. To image the shape of the micropores by FESEM (6700; JEOL, Tokyo, Japan), a 20- to 30-nm-thick carbon film was evaporated on an unbonded and undiced base wafer. Brightfield images taken by a 100× oil-immersion 1.40 NA objective (Olympus, Center Valley, Pa.) were used to measure the micropore width. The depth was measured with a XYZ automated microscope stage (MS2000; Applied Scientific Instrumentation, Eugene, Oreg.) on a Nikon TE2000 microscope. Multiple measurements by two different users were averaged together to produce the relationship between mask distance and micropore width or height (depth). All curves were fitted using a weighted least-squares Marquardt-Levenberg algorithm in Origin Pro 7.0 (OriginLab, Northampton, Mass.).

Cell Culture and Reagents

Biological cells were used as exemplary particles in the Examples provided herein. However, in accordance with the present invention a "particle" may be natural or synthetic chemicals or biological entities. Chemicals and biological entities (biomolecules) include industrial polymers, powders, latexes, emulsions, colloids, environmental pollutants, pesticides, insecticides, drugs such as cocaine and antibiotics, magnetic particles, high-magnetic-permeability particles, metal ions, metal ion complexes, inorganic ions, inorganic ion complexes, organometallic compounds, metals including aluminum, arsenic, cadmium, chromium, selenium, cobalt, copper, lead, silver, nickel, and mercury, and the like, amino acids, peptides, proteins, glycoproteins, nucleotides, nucleic acid molecules, carbohydrates, lipids, lectins, cells, viruses, viral particles, bacteria, organelles, spores, protozoa, yeasts, molds, fungi, pollens, diatoms, toxins, biotoxins, hormones, steroids, immunoglobulins, antibodies, supermolecular assemblies, ligands, catalytic particles, zeolites, and the like, biological and chemical warfare agents, agents used in explosives, and the like.

The mouse macrophage cell line RAW 264.7 was grown on non-treated sterile flasks and maintained in growth media: 0.87×DMEM supplemented with 1:100 Penicillin/Streptomycin, 2 mM L-glutamine, 10% FBS, and 20 mM HEPES. The RG16 cell line stably expressing RelA-GFP was generated as described previously. See Perroud et al. (2008) Anal. Chem. 80:6365-6372, which is herein incorporated by reference. Macrophages were challenged with 1 μM smooth $E.$ $coli$ lipopolysaccharide (L4524) in growth media. 10-μm-diameter polystyrene beads were purchased from Duke Scientific (4210A; Microgenics, Fremont, Calif.). Two different formulations were used for the oil phase: (1) a blend of 60% (w/w) 20-centistoke PDMS oil (378348) and 40% (w/w) Dow Corning Formulation Aid DC5225C; (2) mineral oil (M3516) with 4.5% (v/v) Span 80 (S6760), 0.4% (v/v) TWEEN 80 (P8074), and 0.05% (v/v) Triton X-100 (T9284). The aqueous phase was buffered with PBS.

Bacteria encapsulation experiments were performed with fixed $E.$ $coli$ (K-12 strain) labeled with Alexa Fluor 488 (E-13231; Invitrogen, Carlsbad, Calif.), diluted to about $10^7$ cells/ml. Prior to their first use, the glass microchannels were rendered hydrophobic by flushing the channels with a 5 mM solution of octadecyl-trichlorosilane (AC14740; Acros Organics, Geel, Belgium) in n-hexadecane (AC12046; Acros Organics) for 15 minutes. The coating solution was then flushed from the microchannels with pure n-hexadecane, followed by isopropanol for 5 minutes each. Unless specified, all reagents were purchased from Sigma-Aldrich (St. Louis, Mo.).

EXAMPLE 1

Continuous-Flow Particle Concentration

In a microTAS device, each cell handling functionality is designed to operate optimally at a specific cell density. The ability to control the concentration of cells on-chip mitigates the "concentration mismatch" between integrated components. Additionally, a higher cell concentration enables shorter reaction times, reduced reagent volumes, and higher detection limits for certain applications. The continuous concentration of particles is generally preferred to a trap-and-release strategy when integrating with other on-chip components. Continuous-flow concentration techniques reported in the literature use electrokinetic effects. See Cabrera & Yager (2001) Electrophoresis 22:355-362; and Barrett et al. (2005) Anal. Chem. 77:6798-6804, which are herein incorporated by reference.

Figure 7A:
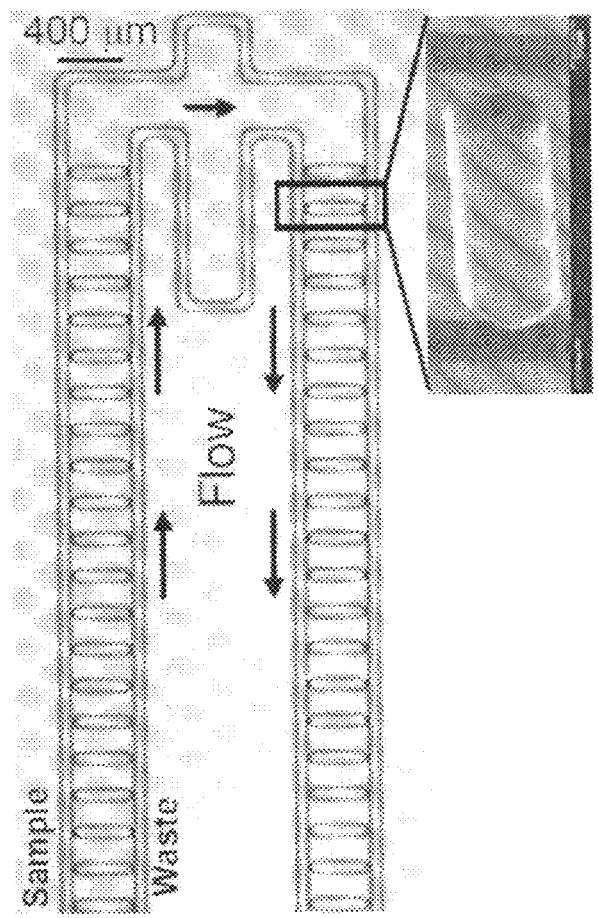
Figure 7B:
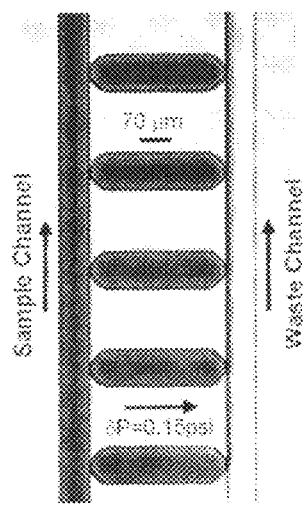
Figure 7C:
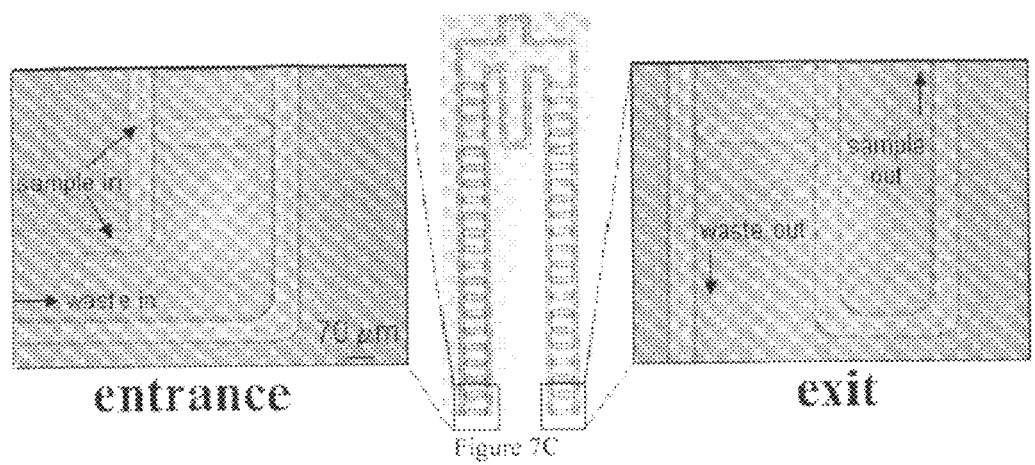

The micropores according to the present invention may be used for microsieving. See Sethu et al. (2006) Lab on a Chip 6:83-89, which is herein incorporated by reference. In particular, a carrier fluid containing particles may be progressively withdrawn through a series of micropores according to the present invention, thereby effectively concentrating the particles. For example, FIG. 7A shows an example of a concentrator of the present invention. The concentrator comprises two congruent channels in parallel (sample and waste) bridged by a series of shunts. The concentrator has 44 shunts, however, the number of shunts may be readily modified according to the degree of concentration one desires. For example, the concentrator may comprise one or more shunts and the maximum number of shunts is only limited by design and space constraints of a given microfluidic device. Each shunt is about a 330-μm-long channel terminated at each end by about a 31-μm-wide 5-μm-deep micropore in a point-to-edge configuration (60-μm mask distance, inset of FIG. 7A). The concentrator was operated by applying a pressure differential, $\Delta P$, between the inlet and outlet fluid reservoirs and another pressure differential, $\delta P$, between the sample and waste legs. The induced transverse flow, $\delta Q$, from the sample leg to the waste leg in the concentrator is visualized in FIG. 7B, where small fractions of tracer dye were successively withdrawn through each shunt ($\Delta P$=2 psi, $\delta P$=0.15 psi). For example, FIG. 7C shows the entrance of the concentrator where beads are far apart from each other and have fast velocities and the exit of the concentrator where beads are closer to each other and have lower velocities. Smaller distances between successive polystyrene beads in conjunction with smaller bead velocities at the exit demonstrated effective concentration of the suspension of particles (initial concentration $1\times10^5$ leads/ml; final concentration about $4\times10^5$ beads/ml).

Figure 7D:
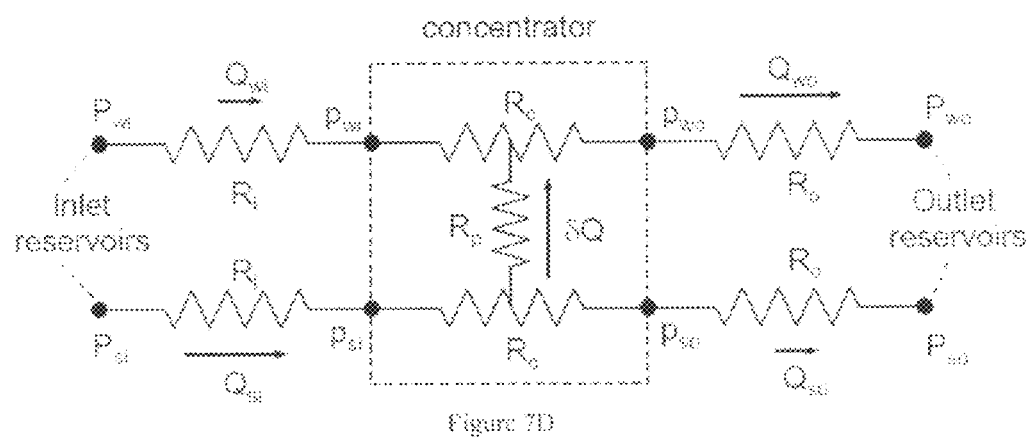

The concentration factor that can be achieved for a given number of micropores can be predicted based on a simple flow circuit model as shown in FIG. 7D. As shown, the model has seven flow resistors. Given the symmetry of the design, a pair of upstream resistors, $R_i$, connect the concentrator to the inlet reservoirs, a pair of downstream resistors, $R_o$, connect the concentrator to the outlet reservoirs, and a pair of resistors, $R_c$, represent the sample and waste legs of the concentrator. An additional resistor accounts for the shunts connecting these two legs and has a combined resistance, $R_p$. The pressures in the reservoirs are designated as $P_j$, where the subscript j has values of si and wi, so and wo representing the sample and waste inlet reservoirs, and the sample and waste outlet reservoirs, respectively. The pressures at the entrance and exit of the concentrator are designated as $p_j$, where the subscript j takes on similar values and meanings as described above. Assuming fully developed steady-state flow, the relationships between the pressures, flow rates, and resistances are given by Equations 1.4 to 1.7 as follows:

$$P_{si}-p_{si}=R_iQ_{si} \quad \text{Eq. 1.4}$$

$$p_{so}-P_{so}=R_oQ_{so} \quad \text{Eq. 1.5}$$

$$P_{wi}-p_{wi}=R_iQ_{wi} \quad \text{Eq. 1.6}$$

$$p_{wo}-P_{wo}=R_oQ_{wo} \quad \text{Eq. 1.7}$$

The applied pressure differentials $\delta P$ and $\Delta P$ result in pressure differentials, $\delta p_i$ and $\delta p_o$, between the sample and waste at the entrance and exit of the concentrator, respectively. This in turn drives the transverse flow, $\delta Q$, from the sample leg to the waste leg in the concentrator as given by Equation 1.8:

$$(\delta p_i + \delta p_o) = 2R_p \delta Q. \quad \text{Eq. 1.8}$$

It is assumed that the driving pressure for this cross flow may be characterized by the average of the pressure differentials at the entrance and exit of the concentrator. From Equations 1.4-1.8 and the definitions of $\delta p_i = p_{si} - p_{wi}$ and $\delta p_o = p_{so} - p_{wo}$, the transverse flow, $\delta Q$, can be expressed by Equation 1.9:

$$\delta Q = \frac{2\delta P}{R_l + R_o + 2R_p} \quad \text{Eq. 1.9}$$

Also, Equation 1.10 for the total flow, $\Sigma Q = Q_{si} + Q_{wi} = Q_{so} + Q_{wo}$, can be derived as:

$$\Sigma Q = \frac{2\Delta P}{R_i + R_o + R_c} \quad \text{Eq. 1.10}$$

Finally, the concentration factor defined as the ratio of the inlet sample flow rate to the outlet sample flow rate, i.e. $\eta = Q_{si}/Q_{so}$, can be expressed as Eq. 1.11:

$$\eta = \frac{\Sigma Q + \delta Q}{\Sigma Q - \delta Q} \quad \text{Eq. 1.11}$$

Figure 7E:
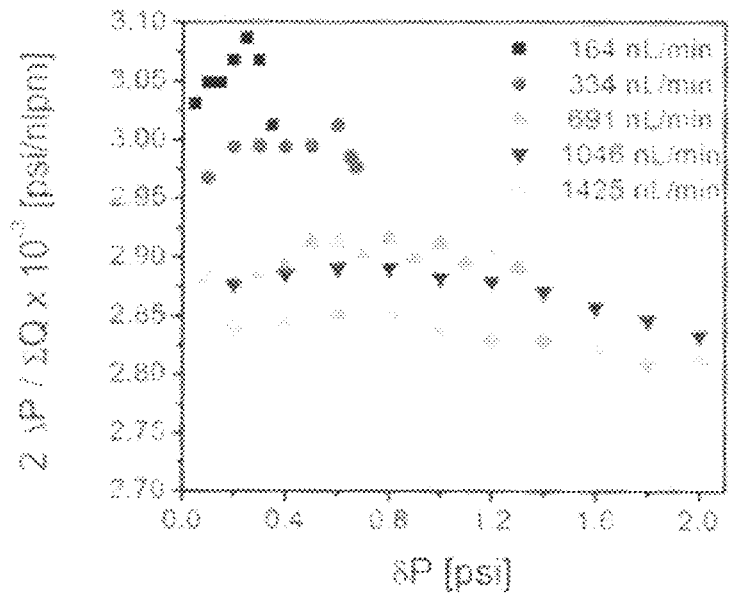
Figure 7F:
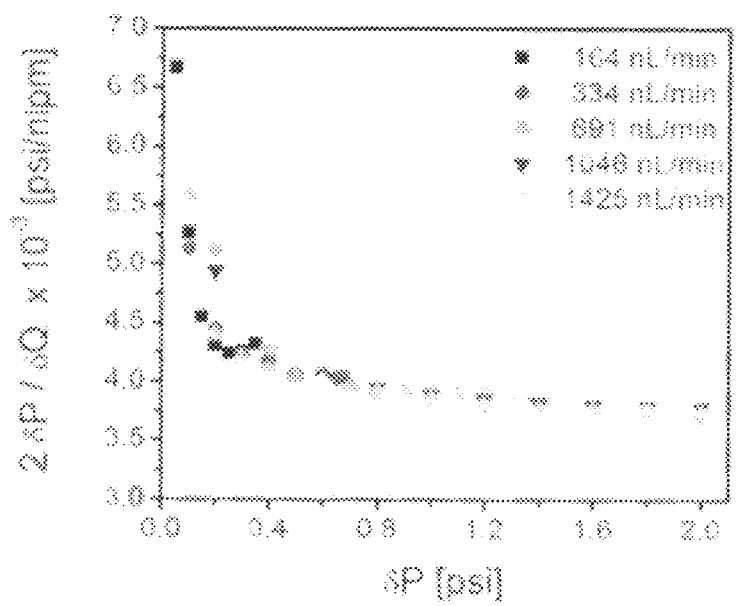

The value for the concentrator leg resistance, $R_c = 8.63 \times 10^{-4}$ psi/nlpm (nlpm=nanoliter per minute), was obtained using a finite volume modeling as described previously. See Harnett et al. (2008) Lab on a Chip 8:565-572, which is herein incorporated by reference. A similar value was also obtained using an analytical expression for flow through a rectangular channel. See White, Viscous Fluid Flow, McGraw-Hill, New York, N.Y., 2006, which is herein incorporated by reference. Values for the resistances $R_i + R_o$ and $R_p$ were determined empirically based on measurements of $\delta Q$ and $\Sigma Q$ for a wide range of $\delta P$ and $\Delta P$ values. This data shows that $2\Delta P/\Sigma Q = R_i + R_o + R_c$ is nearly independent of $\delta P$ and $\Delta P$ and equal to $2.90 \times 10^{-3}$ psi/nlpm. See FIG. 7E. Similarly, the data shows that $2\delta P/\delta Q = R_i + R_o + 2R_p$ can be approximated as a constant, $4.19 \times 10^{-3}$ psi/nlpm, if the data points at small $\delta P$ are excluded. See FIG. 7F. From these values and $R_c = 8.63 \times 10^{-4}$ psi/nlpm, one obtains $R_i + R_o = 2.04 \times 10^{-3}$ psi/nlpm and $R_p = 1.08 \times 10^{-3}$ psi/nlpm. The value determined for $R_i + R_o$ by this empirical method are in agreement with analytical estimates based on the microchannels connecting the concentrator to the chip via holes, and the tubing connecting the chip to the fluid reservoirs. Also note that only this set of resistance values were used in Equations 1.9-1.11 to make predictions for the concentration factor over a wide range of operating conditions.

The concentration factor, $\eta$, was experimentally determined by measuring flow rates at the sample and waste outlets using two matched flow sensors. Both measured and predicted concentration factors are plotted as a function of the pressure differential $\delta P$ for 5 different total flow rates $\Sigma Q$. See FIG. 7G. For a given $\delta P$, the measured concentration factors become larger than the predicted values, and this difference increases with increasing $\delta P$. This systematic discrepancy can be attributed to the variation in $2\delta P/\delta Q = R_i + R_o + 2R_p$, which decreases with increasing $\delta P$ according to the experimental data, while it is assumed to be a constant in the model. See FIG. 7F. If this variation was accounted for in the model, the predictions would be in better agreement with the experiments. Nevertheless, the predictions for the concentration factor obtained from Equations 1.9-1.11 are overall in good agreement with the measured experimental data. From a practical point-of-view, concentration factors above 10 are not preferred since a significant fraction of liquid is withdrawn from the sample by each shunt and particles could potentially clog the micropores, which in turn would increase the pressure differential $\delta P$ on the remaining shunts which would then increase their likelihood of also being clogged.

The capability to precisely control the dimensions of the micropores is important to the performance of the concentrator for a number of reasons. First, the micropores must be very small to create a large flow resistance ($R_p$) so that the pressures in the waste and sample channels do not equilibrate and a transverse flow, $\delta Q$, is maintained. Second, while the design fabricated here performed well, an optimized design would require that the micropores have a size that depends on their location in the concentrator. That is, based on detailed finite volume modeling the pressure difference across the micropores was not the same for all, where it was larger for those micropores located near the inlet and outlet of the concentrator. Consequently, a design that results in the same flow rate through every micropore requires that those micropores be smaller than the micropores in the middle of the concentrator. The flow rate through a micropore is sensitive to its size and shape so a precision fabrication method is essential for an optimized design.

The example above uses individual shunts to remove liquid and concentrate cell. Alternatively, the edge-to-edge mask design can be used to make a continuous horizontal slit with the height small enough to remove liquid but prevent a particle such as a cell from passing. See FIGS. 4G, 6B. This approach is advantageous in that it prevents undesired clogging and pore occlusion and increase the total area for fluid removal. The increased area allows the gradually exchange the initial carrier fluid with a second exchange solution. Controlled fluid exchange is important in cell handling procedures to prevent unwanted shock to cellular function and help preserve internal mechanism. The continuous fluid flow in this design keeps individual cells in constant motion helping to minimize cell-wall adhesion and cell-cell aggregation.

EXAMPLE 2

Micropores as Hydrodynamic Confinement Traps

Single-cell analysis requires tools to transport, immobilize, and image individual cells efficiently. Several microfluidic techniques have been developed to transport and immobilize single cells in an array, but none rivals the simplicity and efficiency of hydrodynamic confinement. These approaches include: (1) dielectrophoretic trapping, which confines cells in a potential well created by electrodes but involves complicated chip fabrication processes; (2) holographic optical trapping limited by a low throughput and by the induced photodamage on the cell after an extended period of time; (3) microwell trapping characterized by a random and slow cell loading step given its reliance on gravitational forces. See Voldman et al. (2002) Anal. Chem. 74:3984-3990; Fuchs et al. (2006) Lab on a Chip 6:121-126; Flynn et al. (2002) Sensors and Actuators B-Chemical 87:239-243; Neuman et al. (1999) Biophysical Journal 77:2856-2863; Inoue et al. (2001) Lab on a Chip 1:50-55; and Deutsch et al. (2006) Lab on a Chip 6:995-1000, which are herein incorporated by reference. Prior art hydrodynamic traps include dam structures, 2-μm by 2-μm cross-section channels, and 2-μm gaps. See Yang et al. (2002) Anal. Chem. 74:3991-4001; Lee et al. (2005) Applied Physics Letters 86:223902-223901, and Di Carlo et al. (2006) Anal. Chem. 78:4925-4930, which are herein incorporated by reference.

According to the present invention, however, the hydrodynamic trap can be a micropore formed by "folding" a 70-μm-wide channel such that two of its corners are overlapping. See FIG. 8A. FIG. 8B shows micrograph of a single mouse macrophage cell immobilized in a 20-μm-wide 6-μm-deep micropore which is imaged by Nomarski differential interference contrast microscopy.

Figure 8C:
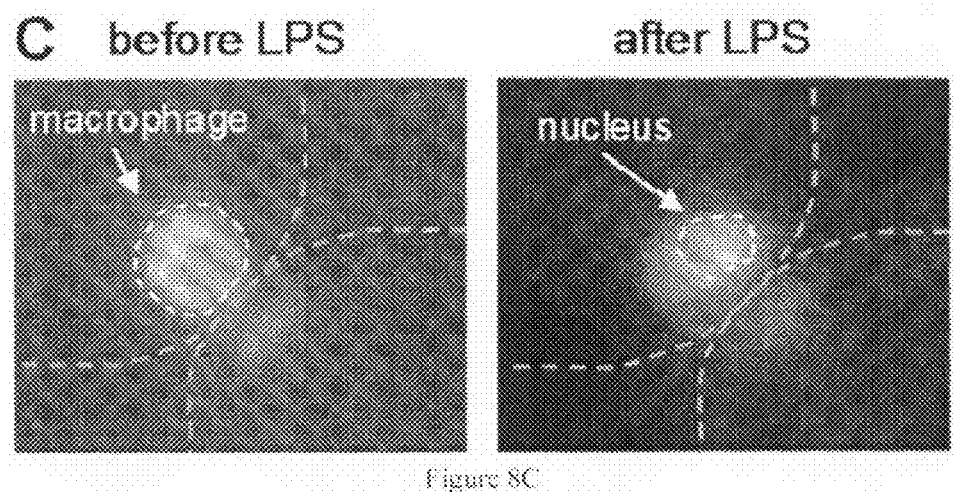

As an example of the various assays that can be conducted on single particles, such as cells, trapped by micropores, the nuclear translocation of nuclear factor kappa-B (NF-κB) in the mouse macrophages was imaged and observed. The nuclear translocation was induced by lipopolysaccharide (LPS). Nuclear translocation of NF-κB was monitored by tagging its RelA subunit with GFP in a stably transfected macrophage cell line using methods known in the art. FIG. 8C shows the fluorescent images of RelA for three representative single macrophage cells captured in a micropore. In order to optimize the signal-to-noise ratio, each captured cell was imaged in PBS before being incubated in growth media with 1 μM LPS for 30 minutes at 37° C. After the LPS challenge, growth media was replaced by PBS and the presence of NF-κB in the nucleus was detected by epi-fluorescence microscopy using methods known in the art. A slight image distortion was observed at the micropore due to the optical interference of the micropore curvature with the fluorescent images of the cells. This distortion may be avoided by imaging the cells from the opposite side of the micropore, where the quartz has a flat surface.

Thus, as exemplified by this example, the micropores according to the present invention may be used as hydrodynamic traps in microfluidic devices to immobilize, manipulate, assay, etc. a single particle, such as a cell.

Figure 8D:
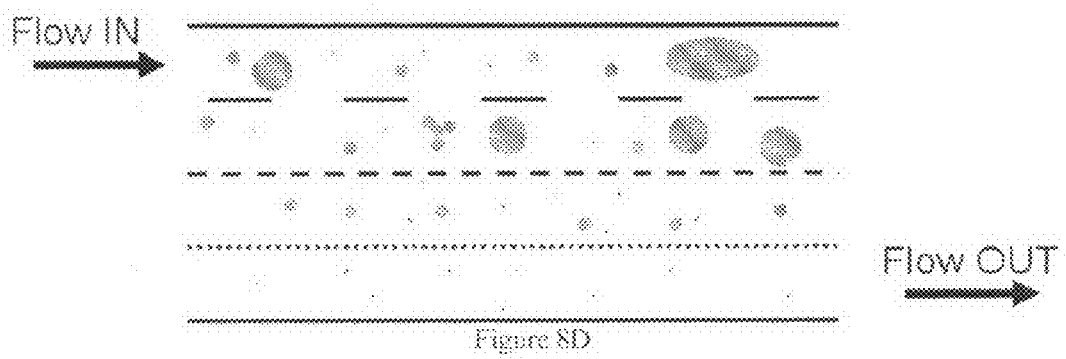
FIG. 8D shows a series of parallel channels connected to each other by a decreasing pore size such that a polydisperse sample can be fractionated.

In some embodiments, a series of micropores, according to the present invention, along a microchannel can be used as a selector or discriminator based on particle size (or shape) allowing smaller-sized particles to be separated from larger ones. One particular example is the separation of single cells from aggregates. FIG. 8D shows a series of parallel channels connected to each other by a decreasing pore size such that a polydisperse sample can be fractionated.

Other applications employing a cell immobilized in the micropore of the present invention include studying or assaying single or multiple ion channels in cells using patch-clamp techniques known in the art.

EXAMPLE 3

Encapsulation of Particles in Picoliter Droplets Generated at a Micropore T-Junction Two-phase droplet-based microfluidic systems have received significant attention for encapsulation of individual cells for high-throughput assays. See Boedicker et al (2008) Lab on a Chip 8:1265-1272; Chabert & Viovy (2008) PNAS USA 105:3191-3196; Edd et al. (2008) Lab on a Chip 8:1262-1264; He et al. (2005) Anal. Chem. 77:1539-1544; and Huebner et al. (2008) Anal. Chem. 80:3890-3896, which are herein incorporated by reference. Two common geometries for continuous generation of picoliter- or nanoliter-sized droplets in microfluidic chips are: the flow-focusing geometry, and the T-junction. In a typical T-junction fabricated by a single-level isotropic wet etch in glass, the width of the dispersed-phase channel is at least twice the depth of the channel. When the width of both of the dispersed-phase and continuous-phase channels are similar, droplets tend to be elongated, and occupy nearly the entire channel width, with only a thin film of the continuous phase wetting the channel walls (so-called "plugs" or "confined" droplets). "Unconfined" droplets are more typically obtained when the dispersed-phase channel is significantly smaller than the continuous-phase channel. See Christopher & Anna, (2007) Journal of Physics D-Applied Physics 40:R319-R336, which is herein incorporated by reference.

Figure 9A:
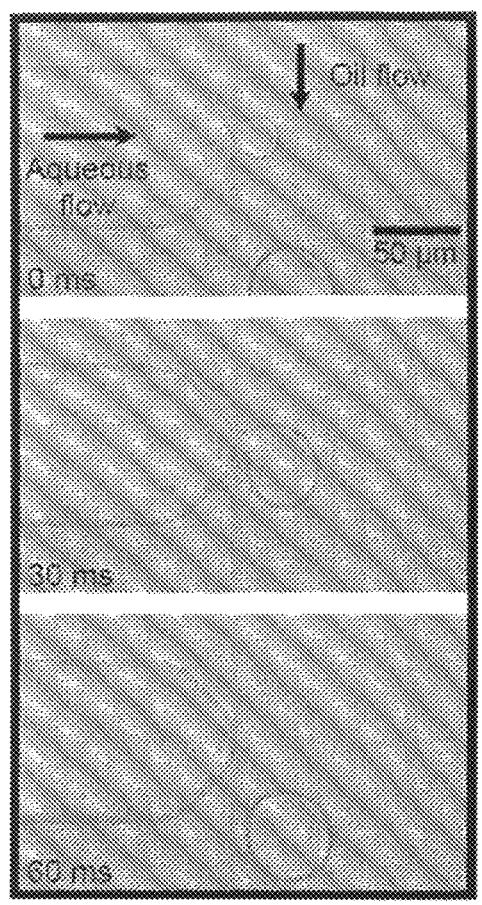
FIGS. 9A-9C show an example of a micropore located at a T-junction to generate picoliter-sized aqueous droplets in an immiscible carrier liquid.

To achieve smaller droplet for a given channel width, a point-to-edge configuration was used to create a micropore T-junction. The micropore T-junction was found to overcome limitations of the prior art by shrinking the size of the channel intersection without decreasing the etch depth, which would otherwise lead to significantly higher pressure drop throughout the chip. FIG. 9A illustrates the formation and breakoff of an aqueous droplet in an immiscible oil using a 40-μm-wide 17-μm-deep micropore T-junction in a 25.03-μm-deep channel (48-μm mask distance). The reduced area of intersection between the dispersed (aqueous) and continuous (oil) streams causes the droplet to be pinched to a narrow "neck" prior to breakoff, without significant interaction with the side walls of the microchannel. In this example, the droplet has a diameter in the channel of about 45 μm, and is partially compressed in the 25-μm-deep channel.

Figure 9B:
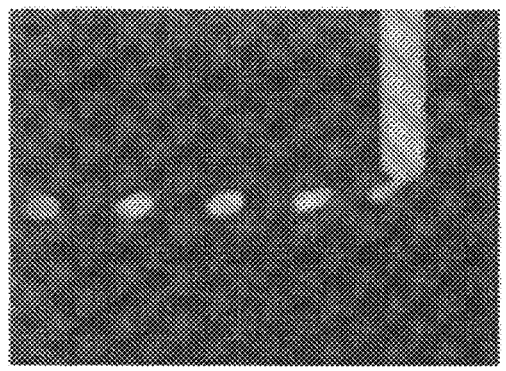

As shown in FIG. 9B, a stream of microdroplets containing a fluorescently labeled protein was continuously generated using the micropore T-junction. The droplet frequency and droplet diameter were controllable by the total flow rate as well as the ratio of flow rates between the two streams. The droplet diameter was about 50% of the full width of the channel, as opposed to alternating "slugs" of fluid that are commonly observed in two-phase flow in microchannels. Addition of surfactant to the oil stream stabilizes the droplets, which allowed off-chip collection and storage. Extended observation suggests that the droplet generation is highly regular and uniform.

Figure 9C:
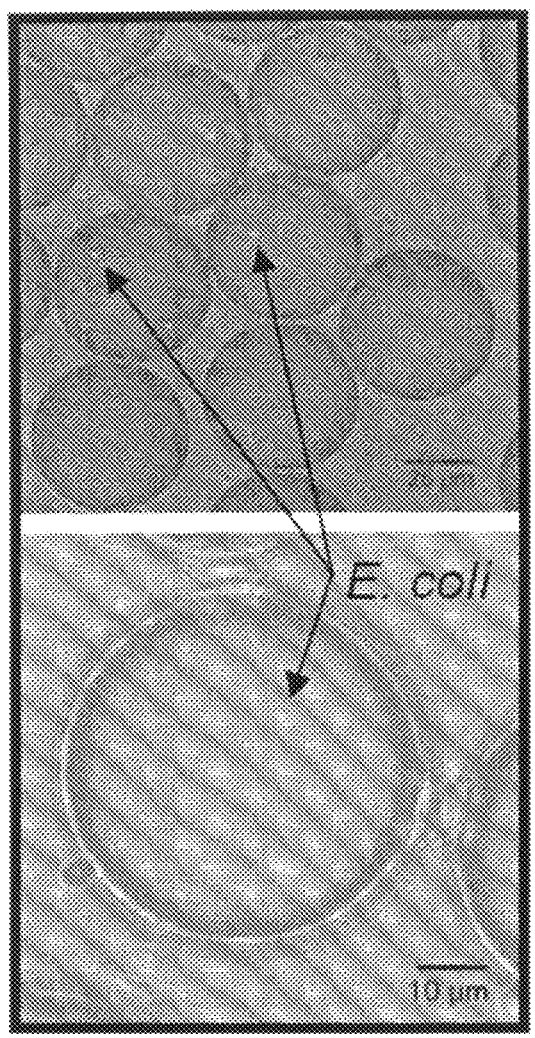

The micropore T-junction was used to encapsulate bacteria, as a first step to performing diagnostic assays such as quantitative PCR on individual cells. See Beer et al. (2007) Anal. Chem. 79:8471-8475, which is herein incorporated by reference. An aqueous suspension of fixed, fluorescently labeled E. coli was fed into an oil stream through a micropore T-junction. The droplets were collected off chip, and imaged by laser-scanning confocal microscopy on a coverslip using methods known in the art. See FIG. 9C. On the coverslip, the droplets presumably adopt a spherical configuration, with a typical diameter of about 50 μm, for a volume of about 65 pL. A single bacterial genome in such a droplet has an effective concentration of about 25 fM, which is two orders of magnitude higher than would be obtained in microfabricated nanoliter reactors previously reported for "digital PCR" assays on individual microbes. See Ottesen (2006) Science 314:1464-1467, which is herein incorporated by reference.

Figure 10A:
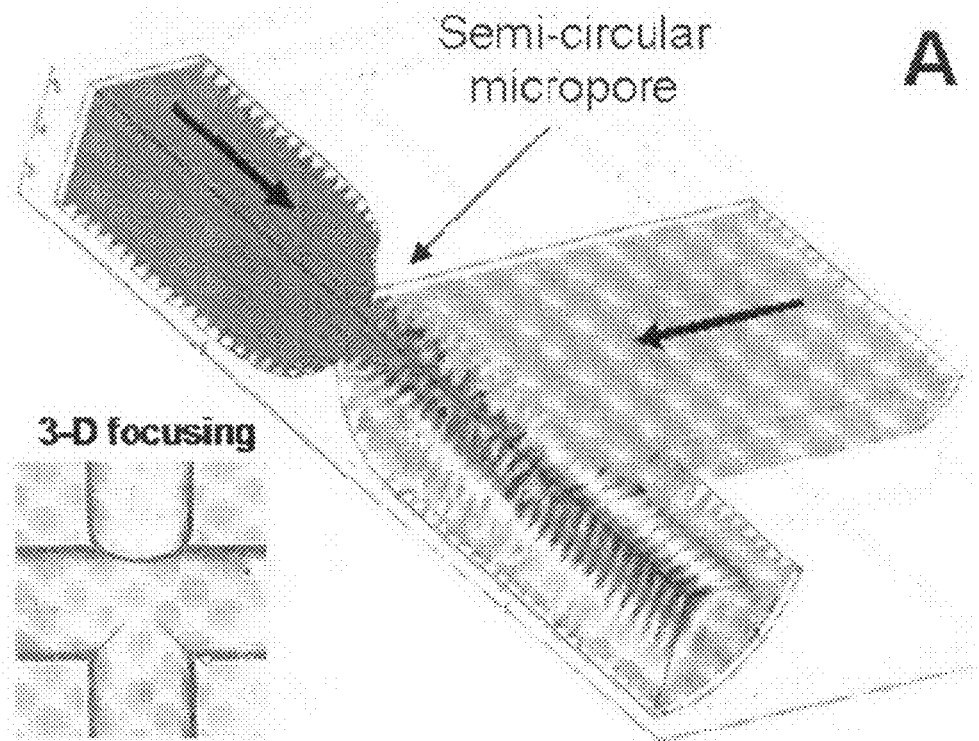
FIGS. 10A-B show an example of a micropore located at a T-junction to generate 3D hydrodynamic focusing.
Figure 10B:
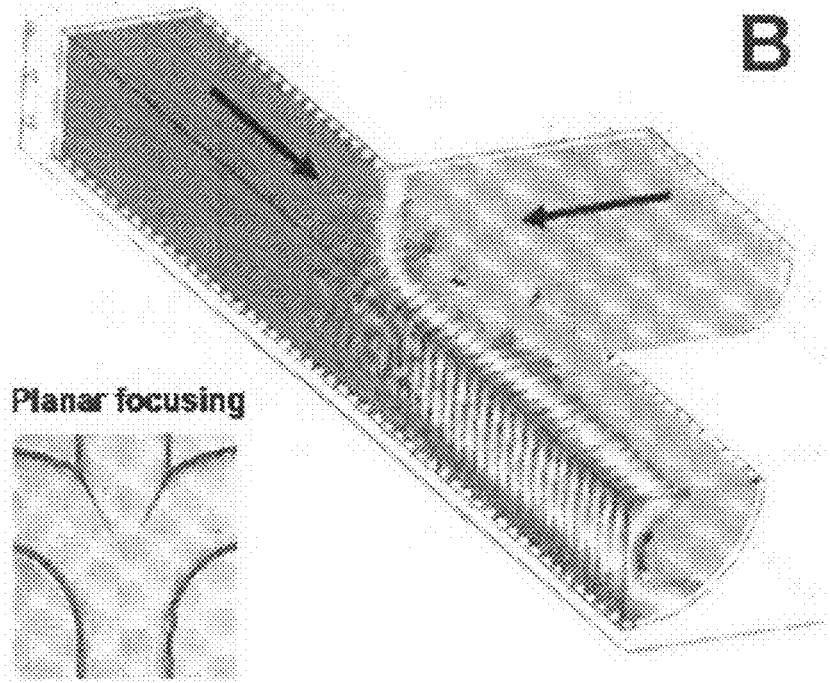

A micropore T-junction can also be used to hydrodynamically focus cells in 3D for flow cytometry, an improvement over planar or 2D hydrodynamic focusing. The particles are hydrodynamically focused in the horizontal plane by two neighboring sheath flows using methods known in the art. At high Reynolds number (Re≈50), the pore focuses the sample vertically against the top wall of the channel, similar to the "smoking chimney" principle. See Wolff et al. (2003) Lab On a Chip 3:22-27, which is herein incorporated by reference. FIG. 10A shows finite element analysis modeling of hydrodynamic focusing at a micropore T-junction (cross-sectional view). FIG. 10B shows that without the micropore at the T-junction, the sample is not focused in the vertical axis.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method for forming a micropore between two isotropic wet etched features in a substrate which comprises
forming the two features by a single-level isotropic wet-etch using an etchant and a mask distance between a mask for each feature that is less than 2× a set etch depth.

2. The method of claim 1, wherein the mask distance is $$g=\sqrt{4\cdot d^2-(2(h-b))^2}$$

wherein d is the set etch depth, h is the desired height of the micropore, and b is a calculated systematic error.

3. The method according to claim 2, wherein the calculated systematic error is calculated by
obtaining measured heights for a plurality of calibration micropores which were formed by single-level isotropic wet etching the features in the substrate with the etchant at the set etch depth and at a plurality of mask distances ranging from about 2× or less the set etch depth; and
using nonlinear regression analysis to fit the measured heights to the following equation $$h_m = \frac{1}{2}\sqrt{4d^2-g^2}+b$$

where $h_m$ is the measured height of the calibration micropore.

4. The method according to claim 3, wherein the plurality of calibration micropores comprises about 15 to 20 calibration micropores.

5. The method of claim 1, wherein the mask distance is
$g=\sqrt{4\cdot d^2-(w-b)^2}$ where the micropore is a point-to-point micropore, or $$g = d + \frac{1}{2}\sqrt{4\cdot d^2-(w-b)^2}$$

where the micropore is a point-to-edge micropore,
wherein d is the set etch depth, w is the desired width of the micropore, and b is a calculated systematic error.

6. The method according to claim 5, where the micropore is the point-to-point micropore, the calculated systematic error is calculated by
obtaining measured widths for a plurality of calibration micropores which were formed by single-level isotropic wet etching the features in the substrate with the etchant at the set etch depth and at a plurality of mask distances ranging from about 2× or less the set etch depth; and
using nonlinear regression analysis to fit the measured widths to the following equation $$w_m=\sqrt{4\cdot d^2-g^2}+b$$

where $w_m$ is the measured width of the calibration micropore.

7. The method according to claim 5, wherein the micropore is the point-to-edge micropore, the calculated systematic error is calculated by
obtaining measured widths for a plurality of calibration micropores which were formed by single-level isotropic wet etching the features in the substrate with the etchant at the set etch depth and at a plurality of mask distances ranging from about 2× or less the set etch depth; and
using nonlinear regression analysis to fit the measured widths to the following equation $$w_m=2\sqrt{(2d-g)g}+b$$

where $w_m$ is the measured width of the calibration micropore.

8. The method according to claim 1, wherein the micropore has a zero thickness.

9. The method according to claim 1, wherein the width of the micropore is about two times the height of the micropore.

10. The method according to claim 1, wherein the micropore is less than about 7 μm in height.

11. The method according to claim 1, which further comprises attaching a cover to the substrate such that the cover forms a wall of the micropore, the features or both.

12. The method of claim 11, wherein the cover comprises a micropore which is aligned over the micropore in the substrate to form a compound micropore having a top portion and a bottom portion.

13. The method according to claim 12, wherein the center of the top portion is centered over the center of the bottom portion or the center of the top portion is off-center over the center of the bottom portion.

14. The method according to claim 12, wherein the top portion and the bottom portion are symmetrical or asymmetrical.

15. The method according to claim 1, wherein the mask distance, the calculated systemic error, or both are calculated with a computer.

* * * * *